United States Patent [19]
Ostrand-Rosenberg et al.

[11] Patent Number: 5,858,776
[45] Date of Patent: Jan. 12, 1999

[54] TUMOR CELLS WITH INCREASED IMMUNOGENICITY AND USES THEREFOR

[75] Inventors: Suzanne Ostrand-Rosenberg, Columbia; Sivasubramanian Baskar, Ellicott City, both of Md.; Laurie H. Glimcher, West Newton, Mass.; Gordon J. Freeman, Brookline, Mass.; Lee M. Nadler, Newton, Mass.

[73] Assignees: Repligen Corporation; Dana-Farber Cancer Institute, both of Boston; President and Fellows of Harvard College, Cambridge, all of Mass.

[21] Appl. No.: 147,772

[22] Filed: Nov. 3, 1993

[51] Int. Cl.$^6$ .............................. C12N 15/09; C12N 5/10; C12N 15/63
[52] U.S. Cl. .................... 435/325; 435/69.1; 435/172.3; 435/320.1; 435/375; 435/354; 435/366
[58] Field of Search ................................ 435/172.3, 69.1, 435/375, 320.1, 325, 354, 366

[56] References Cited

PUBLICATIONS

Ginni et al PNAS 88: 6575, 1991.
Travis Science 259: 310, 1993.
Baskar et al PNAS 90: 5687, 1993.
Chen et al Cell 71: 1093, 1992.
Nabavii et al Nature 360: 266, 1992.
Karl et al EMBO J. 6(6): 1677, 1987.
Clements et al J of Immunology 149(?): 2391, 1992.
Uhlman in Chemical Reviews 90(4): 544, 1990.
Gimmi, C.D. et al. (1993) "Human T–Cell Clonal Anergy is Induced by Antigen Presentation in the Absence of B7 Constimulation" *Proc. Natl. Acad. Sci. USA* 90:6586–6590.
Harding, F.A. et al. (1993) "CD28–B7 Interactions Allow the Induction of CD8$^+$ Cytotoxic T Lymphocytes in the Absence of Exogenous Help" *J. Exp. Med.* 177:1791–1796.
Baskar, S. et al. (1993) "Constitutive Expression of B7 Restores Immunogenicity of Tumor Cells Expressing Truncated Major Histocompatibility Complex Class II Molecules" *Proc. Natl. Acad. Sci. USA* 90:5687–5690.
Ostrand–Rosenberg, S. et al (1993) "Costimulation Through Murine B7 Molecule Restores Immunogenicity of Autologous Tumor Cells Expressing Truncated MHC Class II Molecules" *J. Cell Biochem Supplement* (Abstract HZ 228) p. 71.
Townsend, S.E. et al. (1993) "Expression of the T Cell Costimulatory Ligand B7 By A Melanoma Induces Rejection Mediated By Direct Activation of CD8+ T Cells" *J. Cell Biochem. Supplement* (Abstract NZ 627) p. 136.
Travis, J. (1993) "A Stimulating New Approach to Cancer Treatment" *Science* 259:310–311.
Townsend, S.E. et al. (1993) "Tumor Rejection After Direct Costimulation of CD8$^+$ T Cells by B7–Transfected Melanoma Cells" *Science* 259:368–370.
Tan, P. et al. (1993) "Induction of Alloantigen–Specific Hyporesponsiveness in Human T Lymphocytes by Blocking Interaction of CD28 with Its Natural Ligand B7/BB1" *J. Exp. Med.* 177:165–173.

Chen, L. et al. (1992) "Costimulation of Antitumor Immunity by the B7 Counterreceptor For the T Lymphocyte Molecules CD28 and CTLA–4" *Cell* 71:1093–1102.
Galvin, F. et al. (1992) "Murine B7 Antigen Provides A Sufficient Costimulatory Signal For Antigen–Specific and MHC–Restricted T Cell Activation" *J. Immunology* 149:3802–3808.
Nabavi, N. et al. (1992) "Signalling Through the MHC Class II Cytoplasmic Domain is Required For Antigen Presentation and Induces B7 Expression" *Nature* 360:266–268.
Clements, V.K. et al. (1992) "Invariant Chain Alters The Malignant Phenotype of MHC Class II$^+$ Tumor Cells" *J. of Immunology* 149:2391–2396.
Harding, F.A. et al. (1992) "CD28–Mediated Signalling Co–Stimulates Murine T Cells and Prevents Induction of Anergy in T–Cell Clones" *Nature* 356:607–609.
Reiser, H. et al. (1992) "Murine B7 Antigen Provides an Efficient Costimulatory Signal For Activation of Murine T Lymphocytes Via the T–Cell Receptor/CD3 Complex" *Proc. Natl. Acad. Sci. USA* 89:271–275.
van Der Bruggen, P. et al. (1991) "A Gene Encoding An Antigen Recognized By Cytolytic T Lymphocytes On A Human Melanoma" *Science* 254:1643–1647.
Ostrand–Rosenberg, S. et al. (1991) "Abrogation of Tumorigenicity By MHC Class II Antigen Expression Requires The Cytoplasmic Domain of the Class II Molecule" *J. Immunology* 147:2419–2422.
Gimmi, C.D. et al. (1991) "B–Cell Surface Antigen B7 Provides A Costimulatory Signal That Induces T Cells To Proliferate and Secrete Interleukin 2" *Proc. Natl. Acad. Sci. USA* 88:6575–6579.
Cole, G.A. et al. (1991) "Rejection of Allogeneic Tumor Is Not Determined by Host Responses to MHC Class I Molecules and is Mediated By CD4–CD8$^+$ T Lymphocytes That Are Not Lytic for the Tumor" *Cellular Immunology* 134:480–490.

(List continued on next page.)

*Primary Examiner*—Jasemine C. Chambers
*Assistant Examiner*—Karen M. Hauda
*Attorney, Agent, or Firm*—Lahive & Cockfield, LLP; Amy E. Mandragouras; Megan E. Williams

[57] ABSTRACT

Tumor cells modified to express a T cell costimulatory molecule are disclosed. In one embodiment, the costimulatory molecule is a CD28/CTLA4 ligand, preferably a B lymphocyte antigen B7. The tumor cells of the invention can be modified by transfection with nucleic acid encoding a T cell costimulatory molecule, by using an agent which induces or increases expression of a T cell costimulatory molecule on the tumor cell surface or by coupling a T cell costimulatory molecule to the tumor cell surface. Tumor cells further modified to express MHC class I and/or class II molecules or in which expression of an MHC associated protein, the invariant chain, is inhibited are also disclosed. The modified tumor cells of the invention can be used in methods for treating a patient with a tumor, preventing or inhibiting metastatic spread of a tumor or preventing or inhibiting recurrence of a tumor. A method for specifically inducing a CD4$^+$ T cell response against a tumor and a method for treating a tumor by modification of tumor cells in vivo are disclosed.

18 Claims, 1 Drawing Sheet

PUBLICATIONS

James, R.F.L.(1991) "The Effect of Class II Gene Transfection on the Tumourigenicity of the H–2K–Negative Mouse Leukaemia Cell Line K36.16" *Immunology* 172:213–218.

Bateman, W.J. et al. (1991) "Inducibility of Class II Major Histocompatibility Complex Antigens by Interferon γ is Associated with Reduced Tumorigenicity in C3H Mouse Fibroblasts Transformed by v–Ki–ras" *J. Exp. Med.* 173:193–196.

Freeman, G.J. et al. (1991) "Structure, Expression, and T Cell Costimulatory Activity of the Murine Homologue of the Human B Lymphocyte Activation Antigen B7" *J. Exp. Med.* 174:625–631.

Linsley, P.S. et al. (1991) "Binding of the B Cell Activation Antigen B7 to CD28 Costimulates T Cell Proliferation and Interleukin 2 mRNA Accumulation" *J. Exp. Med.* 173:721–730.

Ostrand–Rosenberg, S. et al. (1990) "Rejection Of Mouse Sarcoma Cells After Transfection of MHC Class II Genes" *J. Immunology* 144:4068–4071.

Fearon, E.R. et al. (1990) "Interleukin–2 Production By Tumor Cells Bypasses T Helper Function in the Generation of An Antitumor Response" *Cell* 60:397–403.

Schultz, K.R. et al. (1990) "The Role of B Cells for In Vivo T Cell Responses to A Friend Virus–Induced Leukemia" *Science* 249:921–923.

Freeman, G.J. (1989) "B7, A New Member of the Ig Superfamily With Unique Expression on Activated And Neoplastic B Cells" *J. Immunology* 143:2714–2722.

Thompson, C.B. et al. (1989) "CD28 Activation Pathway Regulates the Production of Multiple T–Cell–Derived Lymphokines/Cytokines" *Proc. Natl. Acad. Sci USA* 86:1333–1337.

Freedman, A.S. et al. (1987) "B7, A B Cell–Restricted Antigen That Identifies Preactivated B Cells" *J. Immunology* 139:3260–3267.

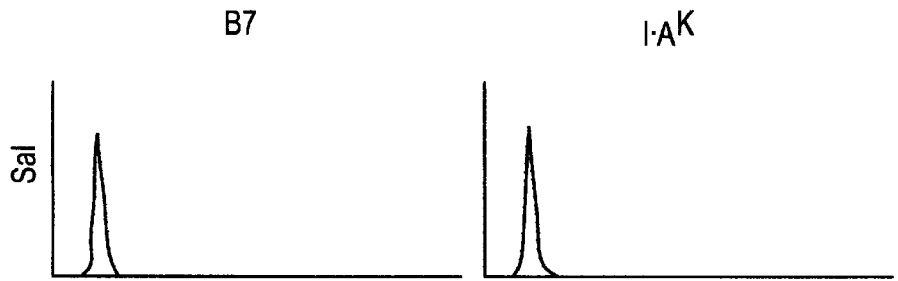
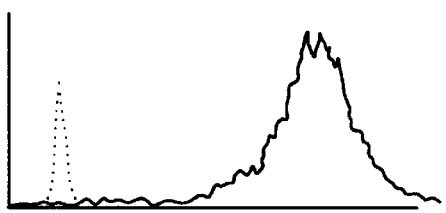
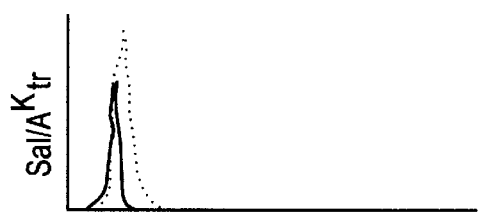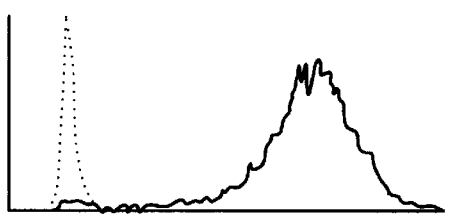
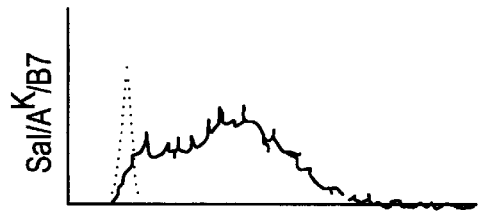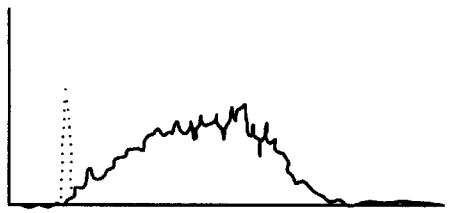

TUMOR CELLS WITH INCREASED IMMUNOGENICITY AND USES THEREFOR

GOVERNMENT FUNDING

Work described herein was supported under grant numbers AI21569, CA52527 and CA40216 awarded by the National Institutes of Health. The U.S. government therefore may have certain rights to this invention.

BACKGROUND OF THE INVENTION

Induction of a T lymphocyte response is a critical initial step in a host's immune response. Activation of T cells results in T cell proliferation, cytokine production by T cells and generation of T cell-mediated effector functions. T cell activation requires an antigen-specific signal, often called a primary activation signal, which results from stimulation of a clonally-distributed T cell receptor (hereafter TcR) present on the surface of the T cell. This antigen-specific signal is usually in the form of an antigenic peptide bound either to a major histocompatibility complex (hereafter MHC) class I protein or an MHC class II protein present on the surface of an antigen presenting cell (hereafter APC). CD4+ T cells recognize peptides associated with class II molecules. Class II molecules are found on a limited number of cell types, primarily B cells, monocytes/macrophages and dendritic cells, and, in most cases, present peptides derived from proteins taken up from the extracellular environment. In contrast, CD8+ T cells recognize peptides associated with class I molecules. Class I molecules are found on almost all cell types and, in most cases, present peptides derived from endogenously synthesized proteins. For a review see Germain, R., *Nature* 322, 687–691 (1986).

It has now been established that, in addition to an antigen-specific primary activation signal, T cells also require a second, non-antigen specific, signal to induce full T cell proliferation and/or cytokine production. This phenomenon has been termed costimulation. Mueller, D. L., et al., *Annu. Rev. Immunol.* 7, 445–480 (1989). Like the antigen-specific signal, the costimulatory signal is triggered by a molecule on the surface of the antigen presenting cell. A costimulatory molecule, the B lymphocyte antigen B7, has been identified on activated B cells and other APCs. Freeman, G. J., et al., *J Immunol.* 139, 3260–3267 (1987); Freeman, G. J., et al., *J Immunol.* 143, 2714–2722 (1989). Binding of B7 to a ligand on the surface of T cells provides costimulation to the T cell. Two structurally similar T cell-surface receptors for B7 have been identified, CD28 and CTLA-4. Aruffo, A. and Seed, B., *Proc. Natl. Acad. Sci. USA* 84, 8573–8577 (1987); Linsley, P. S., et al., *J Exp. Med* 173, 721–730, (1991); Brunet, J. F., et al., *Nature* 328, 267–270 (1987); Brunet, J. F., et al., *Immunol Rev.* 103, 21–36 (1988). CD28 is expressed constitutively on T cells and its expression is upregulated by activation of the T cell, such as by interaction of the TcR with an antigen-MHC complex. In contrast, CTLA4 is undetectable on resting T cells and its expression is induced by activation.

A series of experiments have shown a functional role for a T cell activation pathway stimulated through the CD28 receptor. Studies using blocking antibodies to B7 and CD28 have demonstrated that these antibodies can inhibit T cell activation, thereby demonstrating the need for stimulation via this pathway for T cell activation. Furthermore, suboptimal polyclonal stimulation of T cells by phorbol ester or anti-CD3 antibodies can be potentiated by crosslinking of CD28 with anti-CD28 antibodies. Engagement of the TcR by an MHC molecule/peptide complex in the absence of the costimulatory B7 signal can lead to T cell anergy rather than activation. Damle, N. K., et al., *Proc. Natl. Acad. Sci. USA* 78, 5096–5100 (1981); Lesslauer, W., et al., *Eur. J. Immunol.* 16, 1289–1295 (1986); Gimmi, C. D., et al., *Proc. Natl. Acad. Sci. USA* 88, 6575–6579 (1991); Linsley, P. S., et al., *J Exp. Med.* 173, 721–730 (1991); Koulova, L., et al., *J Exp. Med.* 173, 759–762 (1991); Razi-Wolf, Z., et al., *Proc. Natl. Acad Sci. USA* 89, 4210–4214 (1992).

Malignant transformation of a cell is commonly associated with phenotypic changes in the cell. Such changes can include loss or gain of expression of some proteins or alterations in the level of expression of certain proteins. It has been hypothesized that in some situations the immune system may be capable of recognizing a tumor as foreign and, as such, could mount an immune response against the tumor. Kripke, M., *Adv. Cancer Res.* 34, 69–75 (1981). This hypothesis is based in part on the existence of phenotypic differences between a tumor cell and a normal cell, which is supported by the identification of tumor associated antigens (hereafter TAAs). Schreiber, H., et al. *Ann. Rev. Immunol.* 6, 465–483 (1988). TAAs are thought to distinguish a transformed cell from its normal counterpart. Three genes encoding TAAs expressed in melanoma cells, MAGE-1, MAGE-2 and MAGE-3, have recently been cloned. van der Bruggen, P., et al. *Science* 254, 1643–1647 (1991). That tumor cells under certain circumstances can be recognized as foreign is also supported by the existence of T cells which can recognize and respond to tumor associated antigens presented by MHC molecules. Such TAA-specific T lymphocytes have been demonstrated to be present in the immune repertoire and are capable of recognizing and stimulating an immune response against tumor cells when properly stimulated in vitro. Rosenberg, S. A., et al. *Science* 233, 1318–1321 (1986); Rosenberg, S. A. and Lotze, M. T. *Ann. Rev. Immunol.* 4, 681–709 (1986).

However, in practice, tumors in vivo have generally not been found to be very immunogenic and appear to be capable of evading immune response. This may result from an inability of tumor cells to induce T cell-mediated immune responses. Ostrand-Rosenberg, S., et al., *J Immunol.* 144, 4068–4071 (1990); Fearon, E. R., et al., *Cell* 60, 397–403 (1990). A method for increasing the immunogenicity of a tumor cell in vivo would be therapeutically beneficial.

SUMMARY OF THE INVENTION

Although most tumor cells are thought to express TAAs which distinguish tumor cells from normal cells and T cells which recognize TAA peptides have been identified in the immune repertoire, an anti-tumor T cell response may not be induced by a tumor cell due to a lack of costimulation necessary to activate the T cells. It is known that many tumors are derived from cells which do not normally function as antigen-presenting cells, and, thus, may not trigger necessary signals for T cell activation. In particular, tumor cells may be incapable of triggering a costimulatory signal in a T cell which is required for activation of the T cell. This invention is based, at least in part, on the discovery that tumor cells modified to express a costimulatory molecule, and therefore capable of triggering a costimulatory signal, can induce an anti-tumor T cell-mediated immune response in vivo. This T cell-mediated immune response is effective not only against the modified tumor cells but, more importantly, against the unmodified tumor cells from which they were derived. Thus, the effector phase of the anti-tumor response induced by the modified tumor cells of the invention is not dependent upon expression of a costimulatory molecule on the tumor cells.

Accordingly, the invention pertains to methods of inducing or enhancing T lymphocyte-mediated anti-tumor immunity in a subject by use of a modified tumor cell having increased immunogenicity. In one aspect of the invention, a tumor cell is modified to express a T cell costimulatory molecule on its surface. Prior to modification, the tumor cell may lack the ability to express a T cell costimulatory molecule, may be capable of expressing a T cell costimulatory molecule but fail to do so, or may express insufficient amounts of a T cell costimulatory molecule to activate T cells. Therefore, a tumor cell can be modified by providing a costimulatory molecule to the tumor cell surface, by inducing the expression of a costimulatory molecule on the tumor cell surface or by increasing the level of expression of a costimulatory molecule on the tumor cell surface. In one embodiment, the tumor cell is modified by transfecting the cell with a nucleic acid encoding a T cell costimulatory molecule in a form suitable for expression of the molecule on the cell surface. Alternatively, the tumor cell is contacted with an agent which induces or increases expression of a T cell costimulatory molecule on the cell surface. In yet another embodiment, the tumor cell is modified by chemically coupling a T cell costimulatory molecule to the tumor cell surface.

In a preferred embodiment of the invention, tumor cells are modified to express a molecule which binds CD28 and/or CTLA4 on T lymphocytes. Tumor cells so modified can trigger a signal in T lymphocytes through CD28 and/or CTLA4 to induce T lymphocyte proliferation and/or cytokine production. A preferred molecule which binds CD28 and/or CTLA4 is the B lymphocyte antigen B7. Thus, in one preferred embodiment, a tumor cell is transfected with an expression vector containing a gene encoding B7 in a form suitable for expression of B7 on the cell surface.

Even when provided with the ability to trigger a costimulatory signal in T cells, modified tumor cells may still be incapable of inducing anti-tumor T cell-mediated immune responses due to a failure to sufficiently trigger an antigen-specific primary activation signal. This can result from insufficient expression of MHC class I or class II molecules on the tumor cell surface. Accordingly, this invention encompasses modified tumor cells which provide both a T cell costimulatory signal and an antigen-specific primary activation signal, via an antigen-MHC complex, to T cells. Prior to modification, a tumor cell may lack the ability to express one or more MHC molecules, may be capable of expressing one or more MHC molecules but fail to do so, may express only certain types of MHC molecules (e.g., class I but not class II), or may express insufficient amounts of MHC molecules to activate T cells. Thus, in one embodiment, a tumor cell is modified by providing one or more MHC molecules to the tumor cell surface, by inducing the expression of one or more MHC molecules on the tumor cell surface or by increasing the level of expression of one or more MHC molecules on the tumor cell surface. Tumor cells expressing a T cell costimulatory molecule are further modified, for example, by transfection with a nucleic acid encoding one or more MHC molecules in a form suitable for expression of the MHC molecule(s) on the tumor cell surface. Alternatively, such tumor cells are modified by contact with an agent which induces or increases expression of one or more MHC molecules on the cell.

In a particularly preferred embodiment, tumor cells modified to express a T cell costimulatory molecule are further modified to express one or more MHC class II molecules. To provide an MHC class II molecule, at least one nucleic acid encoding an MHC class II α chain protein and an MHC class II β chain protein are introduced into the tumor cell such that expression of these proteins is directed to the surface of the cell. In yet another embodiment, tumor cells modified to express a costimulatory molecule are further modified to express one or more MHC class I molecules. To provide an MHC class I molecule, at least one nucleic acid encoding an MHC class I α chain protein and a β-2 microglobulin protein are introduced such that expression of these proteins is directed to the surface of the tumor cell. Alternatively, a tumor cell modified to express a costimulatory molecule can be further modified by contact with an agent which induces or increases the expression of MHC molecules (class I and/or class II) on the cell surface.

In certain situations, modified tumor cells of the invention may fail to activate T cells because of insufficient association of TAA-derived peptides with MHC molecules, resulting in a lack of an antigen-specific primary activation signal in T cells. Accordingly, the invention further pertains to a tumor cell modified to trigger a costimulatory signal in T cells and in which association of TAA peptides with MHC class II molecules is promoted in order to induce an antigen-specific signal in T cells. This aspect of the invention is based, at least in part, on the ability of an MHC class II associated protein, the invariant chain, to prevent association of endogenously derived peptides (which would include a number of TAA peptides) with MHC class II molecules intracellularly. Thus, in one embodiment, a tumor cell modified to express a costimulatory molecule is further modified to promote association of TAA peptides with MHC class II molecules by inhibiting the expression of the invariant chain in the tumor cell. The tumor cell selected to be so modified can be one which naturally expresses both MHC class II molecules and the invariant chain or can be one which expresses the invariant chain and which has been modified to express MHC class II molecules. Preferably, expression of the invariant chain is inhibited in a tumor cell by introducing into the tumor cell a nucleic acid which is antisense to a coding or regulatory region of the invariant chain gene. Alternatively, expression of the invariant chain in a tumor cell is prevented by an agent which inhibits expression of the invariant chain gene or which inhibits expression or activity of the invariant chain protein.

The modified tumor cells of the invention can be used in methods for inducing an anti-tumor T lymphocyte response in a subject effective against both modified and unmodified tumor cells. For example, tumor cells can be obtained, modified as described herein to trigger a costimulatory signal in T lymphocytes, and administered to the subject to elicit a T cell-mediated immune response. The modified tumor cells of the invention can also be administered to prevent or inhibit metastatic spread of a tumor or to prevent or inhibit recurrence of a tumor following therapeutic treatment.

This invention also provides methods for treating a subject with a tumor by modifying tumor cells in vivo to be capable of triggering a costimulatory signal in T cells, and, if necessary, also an antigen-specific signal.

The tumor cells of the current invention modified to express both a costimulatory molecule and one or more MHC class II molecules can be used in a method for specifically inducing an anti-tumor response by CD4+ T lymphocytes in a subject with a tumor by administering the modified tumor cells to the subject. Alternatively, a CD4+ T cell response can be induced by modifying tumor cells in vivo to express a costimulatory molecule and one or more MHC class II molecules.

The invention also pertains to a composition of modified tumor cells suitable for pharmaceutical administration. This composition comprises an amount of tumor cells and a physiologically acceptable carrier.

BRIEF DESCRIPTION OF THE DRAWINGS

FIG. 1 shows graphs depicting the cell surface expression of B7 and the MHC class II molecule I-A$^k$ on wild-type and transfected tumor cells as determined by immunofluourescent staining of the cells.

DETAILED DESCRIPTION OF THE INVENTION

The induction of a T cell response requires that at least two signals be delivered by ligands on a stimulator cell to the T cell through cell surface receptors on the T cell. A primary activation signal is delivered to the T cell through the antigen-specific TcR. Physiologically, this signal is triggered by an antigen-MHC molecule complex on the stimulator cell, although it can also be triggered by other means such as phorbol ester treatment or crosslinking of the TcR complex with antibodies, e.g. with anti-CD3. To induce T cell activation, a second signal, called a costimulatory signal, is required by stimulation of the T cell through another cell surface molecule, such as CD28 or CTLA4. Thus, the minimal molecules on a stimulator cell required for T cell activation are an MHC molecule associated with a peptide antigen, to trigger a primary activation signal in a T cell, and a costimulatory molecule to trigger a costimulatory signal in the T cell. Engagement of the antigen-specific TcR in the absence of triggering of a costimulatory signal can prevent activation of the T cell and, in addition, can induce a state of unresponsiveness or anergy in the T cells.

The ability of a tumor cell to evade an immune response and fail to stimulate a T lymphocyte response against the cell may result from the inability of the cell to properly activate T cells. This invention provides modified tumor cells which trigger a costimulatory signal in T cells and, thus, activate an anti-tumor T lymphocyte response. Additionally, in certain embodiments, tumor cells are modified to trigger both a primary, antigen-specific activation signal and a costimulatory signal in T cells. The modified tumor cells of the invention display increased immunogenicity and can be used to induce or enhance a T cell-mediated immune response against a tumor. Since the effector phase of the T cell-mediated immune response is not dependent upon expression of a costimulatory molecule by tumor cells, the T cell-mediated immune response generated by administration of a modified tumor cell of the invention is effective against not only the modified tumor cells but also the unmodified tumor cells from which they were derived.

I. Ex Vivo Modification of a Tumor Cell to Express a Costimulatory Molecule

The inability of a tumor cell to trigger a costimulatory signal in T cells may be due to a lack of expression of a costimulatory molecule, failure to express a costimulatory molecule even though the tumor cell is capable of expressing such a molecule, or insufficient expression of a costimulatory molecule on the tumor cell surface. Thus, according to one aspect of the invention, a tumor cell is modified to express a costimulatory molecule by transfection of the tumor cell with a nucleic acid encoding a costimulatory molecule in a form suitable for expression of the costimulatory molecule on the tumor cell surface. Alternatively, the tumor cell is modified by contact with an agent which induces or increases expression of a costimulatory molecule on the tumor cell surface. In yet another embodiment, a costimulatory molecule is coupled to the surface of the tumor cell to produce a modified tumor cell. The term "costimulatory molecule" is defined herein as a molecule which interacts with a T cell which has received a primary activation signal to result in T cell proliferation and/or cytokine production. Preferred costimulatory molecules include antigens on the surface of B lymphocytes, professional antigen presenting cells (e.g., monocytes, dendritic cells, Langerhans cells) and other cells which present antigen to immune cells (e.g., keratinocytes, endothelial cells, astrocytes, fibroblasts, oligodendrocytes) and which bind either CD28, CTLA4, both CD28 and CTLA4, or other known or as yet undefined receptors on immune cells. A particularly preferred costimulatory molecule which binds CD28 and/or CTLA4 is the B lymphocyte antigen B7.

The ability of a molecule to provide a costimulatory signal to T cells can be determined, for example, by contacting T cells which have received a primary activation signal with the molecule to be tested and determining the presence of T cell proliferation and/or cytokine secretion. T cell can be suboptimally stimulated with a primary activation signal, for instance by contact with immobilized anti-CD3 antibodies or a phorbol ester. Following this stimulation, the T cells are exposed to cells expressing a costimulatory molecule on their surface and the proliferation of the T cells and/or secretion of cytokines, such as IL-2, by the T cells is determined. Proliferation and/or cytokine secretion will be increased by triggering of a costimulatory signal in the T cells. T cell proliferation can be measured, for example, by a standard $^3$H-thymidine uptake assay. Cytokine secretion can be measured, for example, by a standard IL-2 assay. In the case of a costimulatory molecule which is a CD28 ligand, the involvement of CD28 in T cell activation can be demonstrated by the use of blocking antibodies to CD28 which can inhibit T cell proliferation and/or cytokine secretion mediated by this pathway. Linsley, P. S., et al., *J Exp. Med.* 173, 721–730 (1991), Gimmi, C. D., et al., *Proc. Natl. Acad. Sci. USA* 88:, 6575–6579 (1991), Freeman, G. J., et al., *J Exp. Med.* 174, 625–631, (1991).

Fragments, mutants or variants of costimulatory molecules, e.g. CD28 and/or CTLA4 ligands such as B7, that retain the ability to interact with T cells, trigger a costimulatory signal and activate T cell responses, as evidenced by proliferation and/or cytokine production by T cells that have received a primary activation signal, are considered within the scope of the invention. A "fragment" of a costimulatory molecule is defined as a portion of a costimulatory molecule which retains costimulatory activity. For example, a fragment of a costimulatory molecule may have fewer amino acid residues than the entire protein. A "mutant" is defined as a costimulatory molecule having a structural change which may enhance, diminish, not affect, but not eliminate the costimulatory activity of the molecule. For example, a mutant of a costimulatory molecule may have a change in one or more amino acid residues of the protein. A "variant" is defined as a costimulatory molecule having a modification which does not affect the costimulatory activity of the molecule. For example, a variant of a costimulatory molecule may have altered glycosylation or may be a chimeric protein of the costimulatory molecule and another protein.

A. Transfection of a Tumor Cell with a Nucleic Acid Encoding a Costimulatory Molecule Tumor cells can be modified ex vivo to express a T cell costimulatory molecule by transfection of isolated tumor cells with a nucleic acid encoding a costimulatory molecule in a form suitable for expression of the molecule on the surface of the tumor cell. The terms "transfection" or "transfected with" refers to the introduction of exogenous nucleic acid into a mammalian cell and encompass a variety of techniques useful for introduction of nucleic acids into mammalian cells including electroporation, calcium-phosphate precipitation, DEAE-dextran treatment, lipofection, microinjection and infection with viral vectors. Suitable methods for transfecting mammalian cells can be found in Sambrook et al. (*Molecular Cloning: A Laboratory Manual*, 2nd Edition, Cold Spring Harbor Laboratory press (1989)) and other laboratory textbooks. The nucleic acid to be introduced can be, for example, DNA encompassing the gene encoding the costimulatory molecule, sense strand RNA encoding the costimulatory molecule or a recombinant expression vector containing a cDNA encoding the costimulatory molecule. Preferred cDNAs to use are those for human and mouse B7 (Freeman, G. J., et al., *J Exp. Med* 174, 625–631 (1991); Freeman, G. J., et al., *J. Immunol.* 143, 2714–2722 (1989)). The nucleotide sequence of the human B7 cDNA is shown in SEQ ID NO:1 and the corresponding amino acid sequence of the human B7 protein is shown in SEQ ID NO:2. The nucleotide sequence of the mouse B7 cDNA is shown in SEQ ID NO:3 and the corresponding amino acid sequence of the mouse B7 protein is shown in SEQ ID NO:4.

The nucleic acid is "in a form suitable for expression of the costimulatory molecule" in which the nucleic acid contains all of the coding and regulatory sequences required for transcription and translation of a gene, which may include promoters, enhancers and polyadenylation signals, and sequences necessary for transport of the molecule to the surface of the tumor cell, including N-terminal signal sequences. When the nucleic acid is a cDNA in a recombinant expression vector, the regulatory functions responsible for transcription and/or translation of the cDNA are often provided by viral sequences. Examples of commonly used viral promoters include those derived from polyoma, Adenovirus 2, cytomegalovirus and Simian Virus 40, and retroviral LTRs. Regulatory sequences linked to the cDNA can be selected to provide constitutive or inducible transcription, by, for example, use of an inducible promoter, such as the metallothienin promoter or a glucocorticoid-responsive promoter. Expression of the costimulatory molecule on the surface of the tumor cell can be accomplished, for example, by including a native transmembrane coding sequence of the molecule, such as B7, in the nucleic acid sequence, or by including signals which lead to modification of the protein, such as a C-terminal inositol-phosphate linkage, that allows for association of the molecule with the outer surface of the cell membrane.

A preferred approach for introducing nucleic acid encoding a costimulatory molecule into tumor cells is by use of a viral vector containing nucleic acid, e.g. a cDNA, encoding the costimulatory molecule. Examples of viral vectors which can be used include retroviral vectors (Eglitis, M. A., et al., *Science* 230, 1395–1398 (1985); Danos, O. and Mulligan, R., *Proc. Natl. Acad. Sci. USA* 85, 6460–6464 (1988); Markowitz, D., et al., *J Virol.* 62, 1120–1124 (1988)), adenoviral vectors (Rosenfeld, M. A., et al., *Cell* 68, 143–155 (1992)) and adeno-associated viral vectors (Tratschin, J. D., et al., *Mol. Cell. Biol.* 5, 3251–3260 (1985)). Infection of tumor cells with a viral vector has the advantage that a large proportion of cells will receive nucleic acid, thereby obviating a need for selection of cells which have received nucleic acid, and molecules encoded within the viral vector, e.g. by a cDNA contained in the viral vector, are expressed efficiently in cells which have taken up viral vector nucleic acid.

Alternatively, a costimulatory molecule can be expressed on a tumor cell using a plasmid expression vector which contains nucleic acid, e.g. a cDNA, encoding the costimulatory molecule. Suitable plasmid expression vectors include CDM8 (Seed, B., *Nature* 329, 840(1987)) and pMT2PC (Kaufman, et al., *EMBO J* 6, 187–195 (1987)). Since only a small fraction of cells (about 1 out of $10^5$) typically integrate transfected plasmid DNA into their genomes, it is advantageous to transfect a nucleic acid encoding a selectable marker into the tumor cell along with the nucleic acid(s) of interest. Preferred selectable markers include those which confer resistance to drugs such as G418, hygromycin and methotrexate. Selectable markers may be introduced on the same plasmid as the gene(s) of interest or may be introduced on a separate plasmid. Following selection of transfected tumor cells using the appropriate selectable marker(s), expression of the costimulatory molecule on the surface of the tumor cell can be confirmed by immunofluorescent staining of the cells. For example, cells may be stained with a fluorescently labeled monoclonal antibody reactive against the costimulatory molecule or with a fluorescently labeled soluble receptor which binds the costimulatory molecule. Expression of the B7 costimulatory molecule can be determined using a monoclonal antibody, 133, which recognizes B7. Freedman, A. S., et al. *J Immunol.* 139, 3260–3267 (1987). Alternatively, a labeled soluble CD28 or CTLA4 protein or fusion protein which binds to B7 can be used to detect expression of B7.

When transfection of tumor cells leads to modification of a large proportion of the tumor cells and efficient expression of a costimulatory molecule on the surface of tumor cells, e.g. when using a viral expression vector, tumor cells may be used without further isolation or subcloning. Alternatively, a homogenous population of transfected tumor cells can be prepared by isolating a single transfected tumor cell by limiting dilution cloning followed by expansion of the single tumor cell into a clonal population of cells by standard techniques.

B. Induction or Increased Expression of a Costimulatory Molecule on a Tumor Cell Surface A tumor cell can be modified to trigger a costimulatory signal in T cells by inducing or increasing the level of expression of a costimulatory molecule on a tumor cell which is capable of expressing a costimulatory molecule but fails to do so or which expresses insufficient amounts of the costimulatory molecule to activate T cells. An agent which stimulates expression of a costimulatory molecule can be used in order to induce or increase expression of a costimulatory molecule on the tumor cell surface. For example, tumor cells can be contacted with the agent in vitro in a culture medium. The agent which stimulates expression of a costimulatory molecule may act, for instance, by increasing transcription of a costimulatory molecule gene, by increasing translation of a costimulatory molecule mRNA or by increasing stability or transport of a costimulatory molecule to the cell surface. For example, expression of B7 can be upregulated in a cell by a second messenger pathway involving cAMP. Nabavi, N., et al. *Nature* 360, 266–268 (1992). Thus, a tumor cell can be contacted with an agent, which increases intracellular cAMP levels or which mimics cAMP, such as a cAMP analogue, e.g. dibutyryl cAMP, to stimulate expression of B7 on the tumor cell surface. Expression of B7 can also be induced on normal resting B cells by crosslinking cell-surface MHC class II molecules on the B cells with an antibody against the MHC class II molecules. Kuolova, L., et al., *J Exp. Med.* 173, 759–762 (1991). Similarly, a tumor cell which expresses MHC class II molecules on its surface can be treated with anti-MHC class II antibodies to induce or increase B7 expression on the tumor cell surface.

Another agent which can be used to induce or increase expression of a costimulatory molecule on a tumor cell surface is a nucleic acid encoding a transcription factor which upregulates transcription of the gene encoding the costimulatory molecule. This nucleic acid can be transfected into the tumor cell to cause increased transcription of the costimulatory molecule gene, resulting in increased cell-surface levels of the costimulatory molecule.

C. Coupling of a Costimulatory Molecule to the Surface of a Tumor Cell

In another embodiment, a tumor cell is modified to be capable of triggering a costimulatory signal in T cells by coupling a costimulatory molecule to the surface of the tumor cell. For example, a costimulatory molecule, such as B7, can be obtained using standard recombinant DNA technology and expression systems which allows for production and isolation of the costimulatory molecule. Alternatively, a costimulatory molecule can be isolated from cells which express the costimulatory molecule using standard protein purification techniques. For example, B7 protein can be isolated from activated B cells by immunoprecipitation with an anti-B7 antibody such as the 133 monoclonal antibody. The isolated costimulatory molecule is then coupled to the tumor cell. The terms "coupled" or "coupling" refer to a chemical, enzymatic or other means (e.g. antibody) by which a costimulatory molecule is linked to a tumor cell such that the costimulatory molecule is present on the surface of the tumor cell and is capable of triggering a costimulatory signal in T cells. For example, the costimulatory molecule can be chemically crosslinked to the tumor cell surface using commercially available crosslinking reagents (Pierce, Rockford Ill.). Another approach to coupling a costimulatory molecule to a tumor cell is to use a bispecific antibody which binds both the costimulatory molecule and a cell-surface molecule on the tumor cell. Fragments, mutants or variants of costimulatory molecules which retain the ability to trigger a costimulatory signal in T cells when coupled to the surface of a tumor cell can also be used.

II. Additional Modification of a Tumor Cell to Express MHC Molecules

Another aspect of this invention features modified tumor cells which express a costimulatory molecule and which express one or more MHC molecules on their surface to trigger both a costimulatory signal and a primary, antigen-specific, signal in T cells. Before modification, tumor cells may be unable to express MHC molecules, may fail to express MHC molecules although they are capable of expressing such molecules, or may express insufficient amounts of MHC molecules on the tumor cell surface to cause T cell activation. Tumor cells can be modified to express either MHC class I or MHC class II molecules, or both. One approach to modifying tumor cells to express MHC molecules is to transfect the tumor cell with one or more nucleic acids encoding one or more MHC molecules. Alternatively, an agent which induces or increases expression of one or more MHC molecules on tumor cells can be used to modify tumor cells. Inducing or increasing expression of MHC class II molecules on a tumor cell can be particularly beneficial for activating $CD4^+$ T cells against the tumor since the ability of MHC class $II^+$ tumor cells to directly present tumor peptides to $CD4^+$ T cells bypasses the need for professional MHC class $II^+$ APCs. This can improve tumor immunogenicity because soluble tumor antigen (in the form of tumor cell debris or secreted protein) may not be available for uptake by professional MHC class $II^+$ APCs.

One embodiment of the invention is a modified tumor cell which expresses a costimulatory molecule and one or more MHC class II molecules on their cell surface. MHC class II molecules are cell-surface $\alpha/\beta$ heterodimers which structurally contain a cleft into which antigenic peptides bind and which function to present bound peptides to the antigen-specific TcR. Multiple, different MHC class II proteins are expressed on professional APCs and different MHC class II proteins bind different antigenic peptides. Expression of multiple MHC class II molecules, therefore, increases the spectrum of antigenic peptides that can be presented by an APC or by a modified tumor cell. The a and p chains of MHC class II molecules are encoded by different genes. For instance, the human MHC class II protein HLA-DR is encoded by the HLA-DRa and HLA-DR$\beta$ genes. Additionally, many polymorphic alleles of MHC class II genes exist in human and other species. T cells of a particular individual respond to stimulation by antigenic peptides in conjunction with self MHC molecules, a phenomenon termed MHC restriction. In addition, certain T cells can also respond to stimulation by polymorphic alleles of MHC molecules found on the cells of other individuals, a phenomenon termed allogenicity. For a review of MHC class II structure and function, see Germain and Margulies, *Ann. Rev. Immunol.* 11:403–450, 1993.

Another embodiment of the invention is a modified tumor cell which expresses a costimulatory molecule and one or more MHC class I molecules on the cell surface. Similar to MHC class II genes, there are multiple MHC class I genes and many polymorphic alleles of these genes are found in human and other species. Like MHC class II proteins, class I proteins bind peptide fragments of antigens for presentation to T cells. A functional cell-surface class I molecule is composed of an MHC class I $\alpha$ chain protein associated with a $\beta$2-microglobulin protein.

A. Transfection of a Tumor Cell with Nucleic Acid Encoding MHC Molecules Tumor cells can be modified ex vivo to express one or more MHC class II molecules by transfection of isolated tumor cells with one or more nucleic acids encoding one or more MHC class II $\alpha$ chains and one or more MHC class II $\beta$ chains in a form suitable for expression of the MHC class II molecules(s) on the surface of the tumor cell. Both an $\alpha$ and a $\beta$ chain protein must be present in the tumor cell to form a surface heterodimer and neither chain will be expressed on the cell surface alone. The nucleic acid sequences of many murine and human class II genes are known. For examples see Hood, L., et al. *Ann. Rev. Immunol.* 1, 529–568 (1983) and Auffray, C. and Strominger, J. L., *Advances in Human Genetics* 15, 197–247 (1987). Preferably, the introduced MHC class II molecule is a self MHC class II molecule. Alternatively, the MHC class II molecule could be a foreign, allogeneic, MHC class II molecule. A particular foreign MHC class II molecule to be introduced into tumor cells can be selected by its ability to induce T cells from a tumor-bearing subject to proliferate and/or secrete cytokines when stimulated by cells expressing the foreign MHC class II molecule (i.e. by its ability to induce an allogeneic response). The tumor cells to be transfected may not express MHC class II molecules on their surface prior to transfection or may express amounts insufficient to stimulate a T cell response. Alternatively, tumor cells which express MHC class II molecules prior to transfection can be further transfected with additional, different MHC class II genes or with other polymorphic alleles of MHC class II genes to increase the spectrum of antigenic fragments that the tumor cells can present to T cells.

Fragments, mutants or variants of MHC class II molecules that retain the ability to bind peptide antigens and activate T cell responses, as evidenced by proliferation and/or lymphokine production by T cells, are considered within the scope of the invention. A preferred variant is an MHC class II molecule in which the cytoplasmic domain of either one or both of the α and β chains is truncated. Truncation of the cytoplasmic domains allows peptide binding by and cell surface expression of MHC class II molecules but prevents the induction of endogenous B7 expression, which is triggered by an intracellular signal generated by the cytoplasmic domains of the MHC class II protein chains upon crosslinking of cell surface MHC class II molecules. Kuolova. L., et al., *J. Exp. Med.* 173, 759–762 (1991); Nabavi, N., et al. *Nature* 360, 266–268 (1992). In tumor cells transfected to constitutively express B7 or other costimulatory molecule, it may be desirable to inhibit the expression of endogenous B7, for instance to restrain potential downregulatory feedback mechanisms. Transfection of a tumor cell with a nucleic acid(s) encoding a cytoplasmic domain-truncated form of MHC class II α and β chain proteins would inhibit endogenous B7 expression. Such variants can be produced by, for example, introducing a stop codon in the MHC class II chain gene(s) after the nucleotides encoding the transmembrane spanning region. The cytoplasmic domain of either the α chain or the β chain protein can be truncated, or, for more complete inhibition of B7 induction, both the α and β chains can be truncated. See e.g. Griffith et al., *Proc. Natl. Acad. Sci. USA* 85:4847–4852, (1988), Nabavi et al., *J Immunol.* 142:1444–1447, (1989).

Tumor cells can be modified to express an MHC class I molecule by transfection with a nucleic acid encoding an MHC class I α chain protein. For examples of nucleic acids see Hood, L., et al. *Ann. Rev. Immunol.* 1, 529–568 (1983) and Auffray, C. and Strominger, J. L., *Advances in Human Genetics* 15, 197–247 (1987). Optionally, if the tumor cell does not express β-2 microglobulin, it can also be transfected with a nucleic acid encoding the β-2 microglobulin protein. For examples of nucleic acids see Gussow, D., et al., *J Immunol.* 139, 3132–3138 (1987) and Parnes, J. R., et al., *Proc. Natl. Acad. Sci. USA* 78, 2253–2257 (1981). As for MHC class II molecules, increasing the number of different MHC class I genes or polymorphic alleles of MHC class I genes expressed in a tumor cell can increase the spectrum of antigenic fragments that the tumor cells can present to T cells.

When a tumor cell is transfected with nucleic acid which encodes more than one molecule, for example a B7 molecule, an MHC class II α chain protein and an MHC class II β chain protein, the transfections can be performed simultaneously or sequentially. If the transfections are performed simultaneously, the molecules can be introduced on the same nucleic acid, so long as the encoded sequences do not exceed a carrying capacity for a particular vector used. Alternatively, the molecules can be encoded by separate nucleic acids. If the transfections are conducted sequentially and tumor cells are selected using a selectable marker, one selectable marker can be used in conjunction with the first introduced nucleic acid while a different selectable marker can be used in conjunction with the next introduced nucleic acid.

The expression of MHC molecules (class I or class II) on the cell surface of a tumor cell can be determined, for example, by immunoflourescence of tumor cells using fluorescently labeled monoclonal antibodies directed against different MHC molecules. Monoclonal antibodies which recognize either non-polymorphic regions of a particular MHC molecule (non-allele specific) or polymorphic regions of a particular MHC molecule (allele-specific) can be used are known to those skilled in the art.

B. Induction or Increased Expression of MHC Molecules on a Tumor Cell

Another approach to modifying a tumor cell ex vivo to express MHC molecules on the surface of a tumor cell is to use an agent which stimulates expression of MHC molecules in order to induce or increase expression of MHC molecules on the tumor cell surface. For example, tumor cells can be contacted with the agent in vitro in a culture medium. An agent which stimulates expression of MHC molecules may act, for instance, by increasing transcription of MHC class I and/or class II genes, by increasing translation of MHC class I and/or class II mRNAs or by increasing stability or transport of MHC class I and/or class II proteins to the cell surface. A number of agents have been shown to increase the level of cell-surface expression of MHC class II molecules. See for example Cockfield, S. M. et al., *J. Immunol.* 144, 2967–2974 (1990); Noelle, R. J. et al. *J. Immunol.* 137, 1718–1723 (1986); Mond, J. J., et al., *J Immunol.* 127, 881–888 (1981); Willman, C. L., et al. *J. Exp. Med.,* 170, 1559–1567 (1989); Celada, A.and Maki, R. *J. Immunol.* 146, 114–120 (1991) and Glimcher, L. H. and Kara, C. J. *Ann. Rev. Immunol.* 10, 13–49 (1992) and references therein. These agents include cytokines, antibodies to other cell surface molecules and phorbol esters. One agent which upregulates MHC class I and class II molecules on a wide variety of cell types is the cytokine interferon-γ. Thus, for example, tumor cells modified to express a costimulatory molecule can be further modified to increase expression of MHC molecules by contact with interferon-γ.

Another agent which can be used to induce or increase expression of an MHC molecule on a tumor cell surface is a nucleic acid encoding a transcription factor which upregulates transcription of MHC class I or class II genes. Such a nucleic acid can be transfected into the tumor cell to cause increased transcription of MHC genes, resulting in increased cell-surface levels of MHC proteins. MHC class I and class II genes are regulated by different transcription factors. However, the multiple MHC class I genes are regulated coordinately, as are the multiple MHC class II genes. Therefore, transfection of a tumor cell with a nucleic acid encoding a transcription factor which regulates MHC gene expression may increase expression of several different MHC molecules on the tumor cell surface. Several transcription factors which regulate the expression of MHC genes have been identified, cloned and characterized. For example, see Reith, W. et al., *Genes Dev.* 4, 1528–1540, (1990); Liou, H. -C., et al., *Science* 247, 1581–1584 (1988); Didier, D. K., et al., *Proc. Natl. Acad. Sci. USA* 85, 7322–7326 (1988).

III. Inhibition of Invariant Chain Expression in Tumor Cells

Another embodiment of the invention provides a tumor cell modified to express a T cell costimulatory molecule and in which expression of an MHC class II-associated protein, the invariant chain, is inhibited. Invariant chain expression is inhibited to promote association of endogenously-derived TAA peptides with MHC class II molecules to create an antigen-MHC complex. This complex can trigger an antigen-specific signal in T cells to induce activation of T cells in conjunction with a costimulatory signal. MHC class II molecules have been shown to be capable of presenting endogenously-derived peptides. Nuchtern, J. G., et al. *Nature* 343, 74–76 (1990); Weiss, S. and Bogen, B. *Cell* 767–776 (1991). However, in cells which naturally express MHC class II molecules, the α and β chain proteins are associated with the invariant chain (hereafter Ii) during intracellular transport of the proteins from the endoplasmic reticulum. It is believed that Ii functions in part by preventing the association of endogenously-derived peptides with MHC class II molecules. Elliott, W., et al. *J. Immunol.* 138, 2949–2952 (1987); Stockinger, B., et al. *Cell* 56, 683–689 (1989); Guagliardi, L., et al. *Nature (London)* 343, 133–139 (1990); Bakke, O., et al. *Cell* 63, 707–716 (1990); Lottreau, V., et al. *Nature* 348,600–605 (1990); Peters, J., et al. *Nature* 349, 669–676 (1991); Roche, P., et al.*Nature* 345, 615–618 (1990); Teyton, L., et al. *Nature* 348, 39–44 (1990). Since TAAs are synthesized endogenously in tumor cells, peptides derived from them are likely to be available intracellularly. Accordingly, inhibiting the expression of Ii in tumor cells which express Ii may increase the likelihood that TAA peptides will associate with MHC class II molecules. Consistent with this mechanism, it was shown that supertransfection of an MHC class II$^+$, Ii$^-$ tumor cell with the Ii gene prevented stimulation of tumor-specific immunity by the tumor cell. Clements, V. K., et al. *J Immunol.* 149, 2391–2396 (1992).

Prior to modification, the expression of Ii in a tumor cell can be assessed by detecting the presence or absence of Ii mRNA by Northern blotting or by detecting the presence or absence of Ii protein by immunoprecipitation. A preferred approach for inhibiting expression of Ii is by introducing into the tumor cells a nucleic acid which is antisense to a coding or regulatory region of the Ii gene, which have been previously described. Koch, N., et al., *EMBO J* 6, 1677–1683, (1987). For example, an oligonucleotide complementary to nucleotides near the translation initiation site of the Ii mRNA can be synthesized. One or more antisense oligonucleotides can be added to media containing tumor cells, typically at a concentration of oligonucleotides of 200 μg/ml. The antisense oligonucleotide is taken up by tumor cells and hybridizes to Ii mRNA to prevent translation. In another embodiment, a recombinant expression vector is used in which a nucleic acid encoding sequences of the Ii gene in an orientation such that mRNA which is antisense to a coding or regulatory region of the Ii gene is produced. Tumor cells transfected with this recombinant expression vector thus contain a continuous source of Ii antisense nucleic acid to prevent production of Ii protein. Alternatively, Ii expression in a tumor cell can be inhibited by treating the tumor cell with an agent which interferes with Ii expression. For example, a pharmaceutical agent which inhibits Ii gene expression, Ii mRNA translation or Ii protein stability or intracellular transport can be used.

IV. Types of Tumor Cells to be Modified

The tumor cells to be modified as described herein include tumor cells which can be transfected or treated by one or more of the approaches encompassed by the present invention to express a costimulatory molecule. If necessary, the tumor cell can be further modified to express MHC molecules or an inhibitor of Ii expression. A tumor from which tumor cells are obtained can be one that has arisen spontaneously, e.g in a human subject, or may be experimentally derived or induced, e.g. in an animal subject. The tumor cells can be obtained, for example, from a solid tumor of an organ, such as a tumor of the lung, liver, breast, colon, bone etc. Malignancies of solid organs include carcinomas, sarcomas, melanomas and neuroblastomas. The tumor cells can also be obtained from a blood-borne (ie. dispersed) malignancy such as a lymphoma, a myeloma or a leukemia.

The tumor cells to be modified include those that express MHC molecules on their cell surface prior to transfection and those that express no or low levels of MHC class I and/or class II molecules. A minority of normal cell types express MHC class II molecules. It is therefore expected that many tumor cells will not express MHC class II molecules naturally. These tumors can be modified to express a costimulatory molecule and MHC class II molecules. Several types of tumors have been found to naturally express surface MHC class II molecules, such as melanomas (van Duinen et al., *Cancer Res.* 48, 1019–1025, 1988), diffuse large cell lymphomas (O'Keane et al., *Cancer* 66, 1147–1153, 1990), squamous cell carcinomas of the head and neck (Mattijssen et al., *Int. J Cancer* 6, 95–100, 1991) and colorectal carcinomas (Moller et al., *Int. J Cancer* 6, 155–162, 1991). Tumor cells which naturally express class II molecules can be modified to express a costimulatory molecule, and, in addition, other class II molecules which can increase the spectrum of TAA peptides which can be presented by the tumor cell. Most non-malignant cell types express MHC class I molecules. However, malignant transformation is often accompanied by downregulation of expression of MHC class I molecules on the surface of tumor cells. Csiba, A., et al., *Brit. J Cancer* 50, 699–709 (1984). Importantly, loss of expression of MHC class I antigens by tumor cells is associated with a greater aggressiveness and/or metastatic potential of the tumor cells. Schrier, P. I., et al. *Nature* 305, 771–775 (1983); Holden, C. A., et al. *J Am. Acad. Dermatol.* 9., 867–871 (1983); Baniyash, M., et al. *J Immunol.* 129, 1318–1323 (1982). Types of tumors in which MHC class I expression has been shown to be inhibited include melanomas, colorectal carcinomas and squamous cell carcinomas. van Duinen et al., *Cancer Res.* 48, 1019–1025, (1988); Moller et al., *Int. J Cancer* 6, 155–162, (1991); Csiba, A., et al., *Brit. J Cancer* 50, 699–709 (1984); Holden, C. A., et al. *J Am. Acad. Dermatol.* 9., 867–871 (1983). A tumor cell which fails to express class I molecules or which expresses only low levels of MHC class I molecules can be modified by one or more of the techniques described herein to induce or increase expression of MHC class I molecules on the tumor cell surface to enhance tumor cell immunogenicity.

V. Modification of Tumor Cells In Vivo

Another aspect of the invention provides methods for increasing the immunogenicity of a tumor cell by modification of the tumor cell in vivo to express a costimulatory molecule to trigger a costimulatory signal in T cells. In addition, tumor cells can be further modified in vivo to express MHC molecules to trigger a primary, antigen-specific, signal in T cells. Tumor cells can be modified in vivo by introducing a nucleic acid encoding a T cell costimulatory molecule into the tumor cells in a form suitable for expression of the costimulatory molecule on the surface of the tumor cells. Likewise, nucleic acids encoding MHC class I or class II molecules or an antisense sequence of the Ii gene can be introduced into tumor cells in vivo. In one embodiment, a recombinant expression vector is used to deliver nucleic acid encoding B7 to tumor cells in vivo as a form of gene therapy. Vectors useful for in vivo gene therapy have been previously described and include retroviral vectors, adenoviral vectors and adeno-associated viral vectors. See e.g. Rosenfeld, M. A., *Cell* 68, 143–155 (1992); Anderson, W. F., *Science* 226, 401–409 (1984); Friedman, T., *Science* 244, 1275–1281 (1989). Alternatively, nucleic acid can be delivered to tumor cells in vivo by direct injection of naked nucleic acid into tumor cells. See e.g. Acsadi, G., et al., *Nature* 332, 815–818 (1991). A delivery apparatus is commercially available (BioRad). Optionally, to be suitable for injection, the nucleic acid can be complexed with a carrier such as a liposome. Nucleic acid encoding an MHC class I molecule complexed with a liposome has been directly injected into tumors of melanoma patients. Hoffman, M., *Science* 256, 305–309 (1992).

Tumor cells can also be modified in vivo by use of an agent which induces or increases expression of a costimulatory molecule (and, if necessary, MHC molecules as described herein). The agent may be administered systemically, e.g. by intravenous injection, or, preferably, locally to the tumor cells.

VI. The Effector Phase of the Anti-Tumor T Cell-Mediated Immune Response

The modified tumor cells of the invention are useful for stimulating an anti-tumor T cell-mediated immune response by triggering an antigen-specific signal and a costimulatory signal in tumor-specific T cells. Following this inductive, or afferent, phase of an immune response, effector populations of T cells are generated. These effector T cell populations can include both CD4+ T cells and CD8+ T cells. The effector populations are responsible for elimination of tumors cell, by, for example, cytolysis of the tumor cell. Once T cells are activated, expression of a costimulatory molecule is not required on a target cell for recognition of the target cell by effector T cells or for the effector functions of the T cells. Harding, F. A. and Allison, J. P. *J Exp. Med.* 177, 1791–1796 (1993). Therefore, the anti-tumor T cell-mediated immune response induced by the modified tumor cells of the invention is effective against both the modified tumor cells and unmodified tumor cells which do not express a costimulatory molecule.

Additionally, the density and/or type of MHC molecules on the cell surface required for the afferent and efferent phases of a T cell-mediated immune response can differ. Fewer MHC molecules, or only certain types of MHC molecules (e.g. MHC class I but not MHC class II) may be needed on a tumor cell for recognition by effector T cells than is needed for the initial activation of T cells. Therefore, tumor cells which naturally express low amounts of MHC molecules but are modified to express increased amounts of MHC molecules can induce a T cell-mediated immune response which is effective against the unmodified tumor cells. Alternatively, tumor cells which naturally express MHC class I molecules but not MHC class II molecules which are then modified to express MHC class II molecules can induce a T cell-mediated immune response which includes effector T cell populations which can eliminate the parental MHC class I+, class II− tumor cells.

VII. Therapeutic Compositions of Tumor Cells

Another aspect of the invention is a composition of modified tumor cells in a biologically compatible form suitable for pharmaceutical administration to a subject in vivo. This composition comprises an amount of modified tumor cells and a physiologically acceptable carrier. The amount of modified tumor cells is selected to be therapeutically effective. The term "biologically compatible form suitable for pharmaceutical administration . . . in vivo" means that any toxic effects of the tumor cells are outweighed by the therapeutic effects of the tumor cells. A "physiologically acceptable carrier" is one which is biologically compatible with the subject. Examples of acceptable carriers include saline and aqueous buffer solutions. In all cases, the compositions must be sterile and must be fluid to the extent that easy syringability exists. The term "subject" is intended to include living organisms in which tumors can arise or be experimentally induced. Examples of subjects include humans, dogs, cats, mice, rats, and transgenic species thereof.

Administration of the therapeutic compositions of the present invention can be carried out using known procedures, at dosages and for periods of time effective to achieve the desired result. For example, a therapeutically effective dose of modified tumor cells may vary according to such factors as age, sex and weight of the individual, the type of tumor cell and degree of tumor burden, and the immunological competency of the subject. Dosage regimens may be adjusted to provide optimum therapeutic responses. For instance, a single dose of modified tumor cells may be administered or several doses may be administered over time. Administration may be by injection, including intravenous, intramuscular, intraperitoneal and subcutaneous injections.

VIII. Activation of Tumor-specific T Lymphocytes In Vitro

Another approach to inducing or enhancing an anti-tumor T cell-mediated immune response by triggering a costimulatory signal in T cells is to obtain T lymphocytes from a tumor-bearing subject and activate the cells in vitro by contact with a tumor cell and a stimulatory form of a costimulatory molecule. T cells can be obtained from a subject, for example, from peripheral blood. Peripheral blood can be further fractionated to remove red blood cells and enrich for or isolate T lymophocytes or T lymphocyte subpopulations. T cells can be activated in vitro by culturing the T cells with tumor cells obtained from the subject (e.g. from a biopsy or from peripheral blood in the case of blood-borne malignancies) together with a stimulatory form of a costimulatory molecule or, alternatively, by exposure to a modified tumor cell as described herein. The term "stimulatory form" means that the costimulatory molecule is capable of crosslinking its receptor on a T cell and triggering a costimulatory signal in T cells. The stimulatory form of the costimulatory molecule can be, for example, a soluble multivalent molecule or an immobilized form of the costimulatory molecule, for instance coupled to a solid support. Fragments, mutants or variants (e.g. fusion proteins) of costimulatory molecules which retain the ability to trigger a costimulatory signal in T cells can also be used. In a preferred embodiment, a soluble extracellular portion of B7 is used to provide costimulation to the T cells. Following culturing of the T cells in vitro with tumor cells and a costimulatory molecule, or a modified tumor cell, to activate tumor-specific T cells, the T cells can be administered to the subject, for example by intravenous injection.

IX. Therapeutic Uses of Modified Tumor Cells

The modified tumor cells of the present invention can be used to increase tumor immunogenicity, and therefore can be used therapeutically for inducing or enhancing T lymphocyte-mediated anti-tumor immunity in a subject with a tumor or at risk of developing a tumor. A method for treating a subject with a tumor involves obtaining tumor cells from the subject, modifying the tumor cells ex vivo to express a T cell costimulatory molecule, for example by transfecting them with an appropriate nucleic acid, and administering a therapeutically effective dose of the modified tumor cells to the subject. Appropriate nucleic acids to be introduced into a tumor cell include a nucleic acid encoding a T cell costimulatory molecule, for example a CD28 and/or CTLA4 ligand such as B7, alone or together with nucleic acids encoding MHC molecules (class I or class II) or Ii antisense sequences as described herein. Alternatively, after tumor cells are obtained from a subject, they can be modified ex vivo using an agent which induces or increases expression of a costimulatory molecule (and possibly also using agent(s) which induce or increase MHC molecules).

Tumor cells can be obtained from a subject by, for example, surgical removal of tumor cells, e.g. a biopsy of the tumor, or from a blood sample from the subject in cases of blood-borne malignancies. In the case of an experimentally induced tumor, the cells used to induce the tumor can be used, e.g. cells of a tumor cell line. Samples of solid tumors may be treated prior to modification to produce a single-cell suspension of tumor cells for maximal efficiency of transfection. Possible treatments include manual dispersion of cells or enzymatic digestion of connective tissue fibers, e.g. by collagenase.

Tumor cells can be transfected immediately after being obtained from the subject or can be cultured in vitro prior to transfection to allow for further characterization of the tumor cells (e.g. determination of the expression of cell surface molecules). The nucleic acids chosen for transfection can be determined following characterization of the proteins expressed by the tumor cell. For instance, expression of MHC proteins on the cell surface of the tumor cells and/or expression of the Ii protein in the tumor cell can be assessed. Tumors which express no, or limited amounts of or types of MHC molecules (class I or class II) can be transfected with nucleic acids encoding MHC proteins; tumors which express Ii protein can be transfected with Ii antisense sequences. If necessary, following transfection, tumor cells can be screened for introduction of the nucleic acid by using a selectable marker (e.g. drug resistance) which is introduced into the tumor cells together with the nucleic acid of interest.

Prior to administration to the subject, the modified tumor cells can be treated to render them incapable of further proliferation in the subject, thereby preventing any possible outgrowth of the modified tumor cells. Possible treatments include irradiation or mitomycin C treatment, which abrogate the proliferative capacity of the tumor cells while maintaining the ability of the tumor cells to trigger antigen-specific and costimulatory signals in T cells and thus to stimulate an immune response.

The modified tumor cells can be administered to the subject by injection of the tumor cells into the subject. The route of injection can be, for example, intravenous, intramuscular, intraperitoneal or subcutaneous. Administration of the modified tumor cells at the site of the original tumor may be beneficial for inducing local T cell-mediated immune responses against the original tumor. Administration of the modified tumor cells in a disseminated manner, e.g. by intravenous injection, may provide systemic anti-tumor immunity and, furthermore, may protect against metastatic spread of tumor cells from the original site. The modified tumor cells can be administered to a subject prior to or in conjunction with other forms of therapy or can be administered after other treatments such as chemotherapy or surgical intervention.

Another method for treating a subject with a tumor is to modify tumor cells in vivo to express a costimulatory molecule, alone or in conjunction with MHC molecules and/or an inhibitor of Ii expression. This method can involve modifying tumor cells in vivo by providing nucleic acid encoding the protein(s) to be expressed using vectors and delivery methods effective for in vivo gene therapy as described in a previous section. Alternatively, one or more agents which induce or increase expression of a costimulatory molecule, and possibly MHC molecules, can be administered to a subject with a tumor.

The modified tumor cells of the current invention may also be used in a method for preventing or treating metastatic spread of a tumor or preventing or treating recurrence of a tumor. As demonstrated in detail in one of the following examples, anti-tumor immunity induced by B7-expressing tumor cells is effective against subsequent challenge by tumor cells, regardless of whether the tumor cells of the re-exposure express B7 or not. Thus, administration of modified tumor cells or modification of tumor cells in vivo as described herein can provide tumor immunity against cells of the original, unmodified tumor as well as metastases of the original tumor or possible regrowth of the original tumor.

The current invention also provides a composition and a method for specifically inducing an anti-tumor response in $CD4^+$ T cells. $CD4^+$ T cells are activated by antigen in conjunction with MHC class II molecules. Association of peptidic fragments of TAAs with MHC class II molecules results in recognition of these antigenic peptides by $CD4^+$ T cells. Providing a subject with tumor cells which have been modified to express MHC class II molecules along with a costimulatory molecule, or modified in vivo to express MHC class II molecules along with a costimulatory molecule, can be useful for directing tumor antigen presentation to the MHC class II pathway and thereby result in antigen recognition by and activation of $CD4^+$ T cells specific for the tumor cells. As explained in detail in an example to follow, depletion of either $CD4^+$ or $CD8^+$ T cells in vivo, by administration of anti-CD4 or anti-CD8 antibodies, can be used to demonstrate that specific anti-tumor immunity is mediated by a particular (e.g. $CD4^+$) T cell subpopulation.

As demonstrated in Example 2, subjects initially exposed to modified tumor cells develop an anti-tumor specific T cell response which is effective against subsequent exposure to unmodified tumor cells. Thus the subject develops anti-tumor specific immunity. The generalized use of modified tumor cells of the invention from one human subject as an immunogen to induce anti-tumor immunity in another human subject is prohibited by histocompatibility differences between unrelated humans. However, use of modified tumor cells from one individual to induce anti-tumor immunity in another individual to protect against possible future occurrence of a tumor may be useful in cases of familial malignancies. In this situation, the tumor-bearing donor of tumor cells to be modified is closely related to the (non-tumor bearing) recipient of the modified tumor cells and therefore the donor and recipient share MHC antigens. A strong hereditary component has been identified for certain types of malignancies, for example certain breast and colon cancers. In families with a known susceptibility to a particular malignancy and in which one individual presently has a tumor, tumor cells from that individual could be modified to express a costimulatory molecule and administered to susceptible, histocompatible family members to induce an anti-tumor response in the recipient against the type of tumor to which the family is susceptible. This anti-tumor response could provide protective immunity to subsequent development of a tumor in the immunized recipient.

X. Tumor-Specific T Cell Tolerance

In the case of an experimentally induced tumor, such as described in Examples 1 to 3, a subject (e.g. a mouse) can be exposed to the modified tumor cells of the invention before being challenged with unmodified tumor cells. Thus, the subject is initially exposed to TAA peptides on tumor cells together with a costimulatory molecule, which activates TAA-specific T cells. The activated T cells are then effective against subsequent challenge with unmodified tumor cells. In the case of a spontaneously arising tumor, as is the case with human subjects, the subject's immune system will be exposed to unmodified tumor cells before exposure to the modified tumor cells of the invention. Thus, the subject is initially exposed to TAA peptides on tumor cells in the absence of a costimulatory signal. This situation is likely to induce TAA-specific T cell tolerance in those T cells which are exposed to and are in contact with the unmodified tumor cells. Secondary exposure of the subject to modified tumor cells which can trigger a costimulatory signal may not be sufficient to overcome tolerance in TAA-specific T cells which were anergized by primary exposure to the tumor. Use of modified tumor cells to induce anti-tumor immunity in a subject already exposed to unmodified tumor cells may therefore be most effective in early diagnosed patients with small tumor burdens, for instance a small localized tumor which has not metastasized. In this situation, the tumor cells are confined to a limited area of the body and thus only a portion of the T cell repertoire may be exposed to tumor antigens and become anergized. Administration of modified tumor cells in a systemic manner, for instance after surgical removal of the localized tumor and modification of isolated tumor cells, may expose non-anergized T cells to tumor antigens together with a costimulatory molecule, thereby inducing an anti-tumor response in the non-anergized T cells. The anti-tumor response may be effective against possible regrowth of the tumor or against micrometastases of the original tumor which may not have been detected. To overcome widespread peripheral T cell tolerance to tumor cells in a subject, additional signals, such as a cytokine, may need to be provided to the subject together with the modified tumor cells. A cytokine which functions as a T cell growth factor, such as IL-2, could be provided to the subject together with the modified tumor cells. IL-2 has been shown to be capable of restoring the alloantigen-specific responses of previously anergized T cells in an in vitro system when exogenous IL-2 is added at the time of secondary alloantigenic stimulation. Tan, P., et al. *J Exp. Med* 177, 165–173 (1993).

Another approach to generating an anti-tumor T cell response in a subject despite tolerance of the subject's T cells to the tumor is to stimulate an anti-tumor response in T cells from another subject who has not been exposed to the tumor (referred to as a naive donor) and transfer the stimulated T cells from the naive donor back into the tumor-bearing subject so that the transferred T cells can mount an immune response against the tumor cells. An anti-tumor response is induced in the T cells from the naive donor by stimulating the T cells in vitro with the modified tumor cells of the invention. Such an adoptive transfer approach is generally prohibited in outbred populations because of histocompatibility differences between the transferred T cells and the tumor-bearing recipient. However, advances in allogeneic bone marrow transplantation can be applied to this situation to allow for acceptance by the recipient of the adoptively transferred cells and prevention of graft versus host disease. First, a tumor-bearing subject (referred to as the host) is prepared for and receives an allogeneic bone marrow transplant from a naive donor by a known procedure. Preparation of the host involves whole body irradiation, which destroys the host's immune system, including T cells tolerized to the tumor, as well as the tumor cells themselves. Bone marrow transplantation is accompanied by treatment(s) to prevent graft versus host disease such as depletion of mature T cells from the bone marrow graft, treatment of the host with immunosuppressive drugs or treatment of the host with an agent, such as CTLA4Ig, to induce donor T cell tolerance to host tissues. Next, to provide anti-tumor specific T cells to the host which can respond against residual tumor cells in the host or regrowth or metastases of the original tumor in the host, T cells from the naive donor are stimulated in vitro with tumor cells from the host which have been modified, as described herein, to express a costimulatory molecule. Thus, the donor T cells are initially exposed to tumor cells together with a costimulatory signal and therefore are activated to respond to the tumor cells. These activated anti-tumor specific T cells are then transferred to the host where they are reactive against unmodified tumor cells. Since the host has been reconstituted with the donor's immune system, the host will not reject the transferred T cells and, additionally, the treatment of the host to prevent graft versus host disease will prevent reactivity of the transferred T cells with normal host tissues.

This invention is further illustrated by the following examples which should not be construed as limiting. The contents of all references and published patents and patent applications cited throughout the application are hereby incorporated by reference.

In Examples 1–3, mouse sarcoma cells were modified to express the T cell costimulatory molecule B7. The following methodology was used in Examples 1 to 3.

Methods and Materials

A. Cells

SaI tumor cells were maintained as described (Ostrand-Rosenberg, S., et al., *J Immunol.* 144, 4068–4071 (1990)).

B. Antibodies

The monoclonal antibody (mAb) 10–3.6, specific for I-Ak (Oi, V., et al. *Curr. Top. Microbiol. Immunol.* 81, 115–120 (1978)), was prepared and used as described. Ostrand-Rosenberg, S., et al., *J. Immunol.* 144:4068–4071 (1990). The B7-specific mAb 1G10 is a rat IgG2a mAb and was used as described (Nabavi, N., et al. *Nature* 360, 266–268 (1992)). mAbs specific for CD4$^+$ [GK1.5 (Wilde, D. B., et al. *J. Immunol.* 131, 2178–2183 (1983))] and CD8$^+$ [2.43 (Sarmiento, M., et al. *J. Immunol.* 125, 2665–2672 (1980))] were used as ascites fluid.

C. Transfections

Mouse SaI sarcoma cells were transfected as described in Ostrand-Rosenberg, S., et al., *J. Immunol.* 144, 4068–4071 (1990). SaI cells (2×10$^6$) were transfected by the calcium phosphate method (Wigler et al., *Proc. Natl. Acad. Sci. USA.* 76, 1373 (1979)). SaI cells were transfected with wild-type Aα$^k$ MHC class II cDNAs (Ostrand-Rosenberg, S., et al., *J. Immunol.* 144, 4068–4071 (1990)), Aα$^k$ and Aβ$^k$ cDNAs truncated for their C-terminal 12 and 10 amino acids, respectively (Nabavi, N., et al. *J. Immunol.* 142, 1444–1447 (1989)), and/or B7 gene (Freeman, G. J., et al. *J. Exp. Med.* 174, 625–631 (1991)). For transfection, the murine B7 cDNA was subcloned into the eukaryotic expression vector dCDNAI (Invitrogen, San Diego, Calif.). Class II transfectants were cotransfected with pSV2neo plasmid and selected for resistance to G418 (400 µg/ml). All transfectants were cloned twice by limiting dilution, except SaI/B7 transfectants, which were uncloned, and maintained in drug.

Double transfectants were maintained in G418 plus hygromycin. The numbers after each transfectant are the clone designation.

D. Immunofluorescence

Indirect immunofluorescence was performed as described (Ostrand-Rosenberg. S., et al., *J. Immunol.* 144, 4068–4071 (1990)), and samples on an Epics C flow cytometer.

E. Tumor Challenges

For primary tumor challenges, autologous A/J mice were challenged intraperitoneally (i.p.) with the indicated number of tumor cells. Inoculated mice were checked three times per week for tumor growth. Mean survival times of mice dying from their tumor ranged from 13 to 28 days after inoculation. Mice were considered to have died from their tumor if they contained a large volume of ascites fluid and tumor-free cells ($\geq 5$ ml) at the time of death. Mice were considered tumor-resistant if they were tumor-free for at least 60 days after tumor challenge (range, 60–120 days). tumor cells were monitored by indirect immunofluorescence for I-$A^k$ and B7 expression prior to tumor-cell inoculation. For the experiments of table 2, autologous A/J mice were immunized i.p. with a single inoculum of the indicated number of live tumor cells and challenged i.p. with the indicated number of wild-type SaI cells 42 days after immunization. Mice were evaluated for tumor resistance or susceptibility using the same criteria as for primary tumor challenge.

F. In vivo T cell Depletions

A/J mice were depleted of CD4$^+$ or CD8$^+$ T cells by i.p. inculation with 100 $\mu$l of ascites fluid of mAb GK1.5 (CD4$^+$ specific; Wilde, D. B., et al., *J. Immunol.* 131, 2178–2183 (1983)) or mAb 2.43 (CD8$^+$ specfic; Sarmiento, M., et al., *J. Immunol.* 125, 2665–2672 (1980)) on days $-6$, $-3$, and $-1$ prior to tumor challenge, and every third day after tumor challenge as described (Ghobrial, M., et al. *Clin. Immunol. Immunopathol.* 52, 486–506 (1989)) until the mice died or day 28, whichever came first. Presence or absence of tumor as assessed up to day 28. Previous studies have established that A/J mice with large tumors at day 28 after injection will progress to death. This time point was, therefore, chosen to assess tumor susceptibility for the in vivo depletion experiments. One mouse per group was sacrificed on day 28, and its spleen was assayed by immunofluorescence to ascertain depletion of the relevant T cell population.

Example 1
Coexpression of B7 Restores Tumor Immunogenicity

A mouse sarcoma cell line SaI was used in each of the examples. The mouse SaI sarcoma is an ascites-adapted class I$^+$ class II$^-$ tumor of A/J (H-2$K^k A^k D^d$) mice. The wild-type tumor is lethal in autologous A/J mice when administered i.p. It has previously been shown that SaI cells transfected with, and expressing, syngeneic MHC class II genes (A$\alpha^k$ and A$\beta^k$ genes; SaI/$A^k$ cells) are immunologically rejected by the autologous host, and immunization with live SaI/$A^k$ cells protects mice against subsequent challenges with wild-type class II$^-$ SaI cells (Ostrand-Rosenberg, S., et al., *J Immunol.* 144, 4068–4071 (1990)). Adoptive transfer (Cole, G., et al. *Cell. Immunol.* 134, 480–490 (1991)) and lymphocyte depletion studies (E. Lamousse-Smith and S. O. -R., unpublished data) demonstrate that SaI and SaI/$A^k$ rejection is dependent on CD4$^+$ lymphocytes. SaI cells expressing class II molecules with truncated cytoplasmic domains (SaI/$A^k$tr cells), however, are as lethal as wild-type class II$^-$ SaI cells, suggesting that the cytoplasmic region of the class II heterodimer is required to induce protective immunity (Ostrand-Rosenberg, S., et al. *J Immunol.* 147, 2419–2422 (1991)).

Up-regulation of the B7 activation molecule on APCs is triggered by intracellular signals transmitted by the cytoplasmic domain of the class II heterodimer, after presentation of antigen to CD4$^+$T helper cells (Nabavi, N., et al., *Nature* 360, 266–268 (1992)). Inasmuch as B7 expression is normally up-regulated in vivo on SaI cells expressing full-length class II molecules (S. B. and S. O. -R., unpublished data), it may be that SaI/$A^k$tr cells do not stimulate protective immunity because they do not transmit a costimulatory signal.

To test whether B7 expression can compensate for the absence of the class II cytoplasmic domain, SaI/$A^k$tr cells were supertransfected with a plasmid containing a cDNA encoding murine B7 under the control of the cytomegalovirus promoter and screened for I-$A^k$ and B7 expression by indirect immunofluoroscrence. Wild-type SaI cells do not express either I-$A^k$ or B7 (FIG. 1 *a* and *b*), whereas SaI cells transfected with A$\alpha^k$and A$\beta^k$ genes (SaI/$A^k$ cells) express I-$A^k$ (FIG. 1 *d* and *f*) and do not express B7 (FIG. 1 *c* and *e*). SaI cells transfected with truncated class II genes plus the B7 gene (SaI/$A^k$tr/B7 cells) express I-$A^k$ and B7 molecules (FIG. 1 *g* and *h*). All cells express uniform levels of MHC class I molecules ($K^k$ and $D^d$) comparable to the level of I-$A^k$ in FIG. 1 *h*.

Antigen-presenting activity of the transfectants was tested by determining their immunogenicity and lethality in autologous A/J mice. As shown in Table 1, wild-type SaI cells administered i.p. at doses as low as $10^4$ cells are lethal in 88–100% of mice inoculated within 13–28 days after challenge, whereas 100 times as many SaI/$A^k$ cells are uniformly rejected. Challenges with similar quantities of SaI/$A^k$tr cells are also lethal; however, SaI/$A^k$tr cells that coexpress B7 (SaI/$A^k$tr/B7 clones $-1$ and $-3$) are uniformly rejected. A/J mice challenged with SaI/$A^k$tr cells transfected with the B7 construct, but not expressing detectable amounts of B7 antigen (SaI/$A^k$tr/hph cells), are as lethal as SaI/$A^k$tr cells, demonstrating that reversal of the malignant phenotype in SaI/$A^k$tr/B7 cells is due to expression of B7. SaI cells transfected with the B7 gene and not coexpressing truncated class II molecules (SaI/B7 cells, uncloned) are also as lethal as wild-type SaI cells, indicating the B7 expression without truncated class II molecules does not stimulate immunity. To ascertain that rejection of SaI/$A^k$ and SaI/$A^k$tr/B7 cells is immunologically mediated, sublethally irradiated (900 rads; 1 rad=0.01 Gy) A/J mice were challenged i.p. with these cells. In all cases, irradiated mice died from the tumor. Thus, immunogenicity and host rejection of the MHC class II$^+$ tumor cells are dependent on an intact class II molecule and that coexpression of B7 can bypass the requirement of the class II intracellular domain.

TABLE 1

Tumorigenicity of B7 and MHC class II-transfected SaI tumor cells

| Challenge tumor | Expression | | Tumor dose, no. of cells | Mice dead/mice tested, no./no. |
|---|---|---|---|---|
| | I-$A^k$ | B7 | | |
| SaI | — | — | $1 \times 10^6$ | 9/10 |
| | — | — | $1 \times 10^5$ | 8/10 |
| | — | — | $1 \times 10^4$ | 7/8 |
| SaI/$A^k$ 19.6.4 | $A^k$ | — | $1 \times 10^6$ | 0/12 |
| | $A^k$ | — | $5 \times 10^5$ | 0/5 |
| | $A^k$ | — | $1 \times 10^5$ | 0/5 |
| SaI/$A^k$tr 6.11.8 | $A^k$tr | — | $1 \times 10^6$ | 12/12 |
| | $A^k$tr | — | $5 \times 10^5$ | 5/5 |
| | $A^k$tr | — | $1 \times 10^5$ | 5/10 |
| SaI/$A^k$tr/B7-1 | $A^k$tr | B7 | $1 \times 10^6$ | 0/4 |

TABLE 1-continued

Tumorigenicity of B7 and MHC class II-transfected SaI tumor cells

| Challenge tumor | Expression I-A$^k$ | B7 | Tumor dose, no. of cells | Mice dead/mice tested, no./no. |
|---|---|---|---|---|
| SaI/A$^k$tr/B7-3 | A$^k$tr | B7 | $1 \times 10^6$ | 0/5 |
|  | A$^k$tr | B7 | $4 \times 10^5$ | 0/5 |
|  | A$^k$tr | B7 | $1 \times 10^5$ | 0/5 |
| SaI/A$^k$tr/hph | A$^k$tr | — | $1 \times 10^6$ | 5/5 |
| SaI/B7 | — | B7 | $1 \times 10^6$ | 5/5 |

Example 2
Immunization with B7-Transfected Sarcoma Cells Protects Against Later Challenges of Wild-Type B7⁻Sarcoma Activation of at least some T cells is thought to be dependent on coexpression of B7. However, once the T cells are activated, B7 expression is not required on the target T cell for recognition by effector T cells. The ability of three SaI/$^A$ktr/B7 clones (B7-3, B7-1, and B7- 2B5.F2) to immunize A/J mice against subsequent challenges of wild-type class II⁻ B7⁻ SaI cells (Table 2) was determined. A/J mice were immunized with live SaI/A$^k$tr/B7 transfectants and 42 days later challenged with wild-type SaI tumor cells. Ninety-seven percent of mice immunized with SaI/Aktr/B7 transfectants were immune to ≧$10^6$ wild-type B7⁻ class II⁻ SaI cells, an immunity that is comparable to that induced by immunization with SaI cells expressing full-length class II molecules. SaI/A$^k$tr/B7 cells, therefore, stimulate a potent response with long-term immunological memory against high-dose challenges of malignant tumor cells. B7 expression is, therefore, critical for the stimulation of SaI-specific effector cells; however, its expression is not needed on the tumor targets once the appropriate effector T cell populations have been generated.

TABLE 2

Autologous A/J mice immunized with SaI/A$^k$tr/B7 cells are immune to challenges of wild-type SaI tumor

| Immunization | No. of immunizing cells | SaI challenge dose no. of cells | Mice dead/ mice tested no./no. |
|---|---|---|---|
| None | — | $1 \times 10^6$ | 5/5 |
| SaI/A$^k$ 19.6,4 | $1 \times 10^5$ or $10^6$ | $1 \times 10^6$ | 0/5 |
|  | $1 \times 10^6$ | $6 \times 10^6$ | 0/5 |
| SaI/A$^k$tr/B7-3 | $1 \times 10^6$ | $6 \times 10^6$ | 0/5 |
|  | $1 \times 10^6$ | $1 \times 10^6$ | 0/5 |
|  | $4 \times 10^5$ | $1 \times 10^6$ | 0/5 |
|  | $1 \times 10^5$ | $5 \times 10^6$ | 0/5 |
| SaI/A$^k$tr/B7-1 | $5 \times 10^5$ | $3 \times 10^6$ | 0/3 |
|  | $2 \times 10^5$ | $1 \times 10^6$ | 0/2 |
|  | $5 \times 10^4$ | $5 \times 10^6$ | 0/3 |
| SaI/A$^k$tr/B7-2B5.E2 | $1 \times 10^5$ | $2 \times 10^6$ | 0/2 |
|  | $5 \times 10^4$ | $2 \times 10^6$ | 1/7 |

Example 3
Immunization with B7-Transfected Tumor Cells Stimulates Tumor-Specific CD4$^±$ Lymphocytes To ascertain that B7 is functioning through a T cell pathway in tumor rejection, we have in vivo-depleted A/J mice for CD4$^+$ or CD8$^+$ T cells and challenged them i.p with SaI/A$^k$ or SaIA$^k$tr/B7 cells. As shown in Table 3, in vivo depletion of CD4$^+$ T cells results in host susceptibility to both SaI/A$^k$ and SaI/A$^k$tr/B7 tumors, indicating that CD4$^+$ T cells are critical for tumor rejection, whereas depletion of CD8$^+$ T cells does not affect SaI/A$^k$tr/B7 tumor rejection. Although immunofluorescence analysis of splenocytes of CD8$^+$-depleted mice demonstrates the absence of CD8$^+$ T cells, it is possible that the depleted mice contain small quantitites of CD8$^+$ cells that are below our level of detection. These data therefore demonstrate that CD4$^+$ T cells are required for tumor rejection but do not eliminate a possible corequirement for CD8$^+$ T cells.

TABLE 3

Tumor susceptibility of A/J mice in vivo-depleted for CD4$^+$ or CD8$^+$ T cells

| Tumor challenge | Host T cell depletion | No. mice with tumor/ Total no. mice challenged |
|---|---|---|
| SaI/A$^k$ | CD4$^+$ | 3/5 |
| SaI/A$^k$tr/B7-3 | CD4$^+$ | 5/5 |
|  | CD8$^+$ | 0/5 |

Previous adoptive transfer experiments (Cole, G., et al. Cell. Immunol. 134, 480–490 (1991)) have demonstrated that both CD4$^+$ and CD8$^+$ T cells are required for rejection of class II wild-type SaI cells. Inasmuch as rejection of SaI/A$^k$ and SaI/A$^k$tr/B7 cells appears to require only CD4$^+$ T cells, it is likely that immunization with class II$^+$ transfectants stimulates both CD4$^+$ and CD8$^+$ effector T cells; however, only the CD8$^+$ effectors are required for rejection of class I$^+$II$^-$ tumor targets. Costimulation by B7, therefore, enhances immunity by stimulating tumor-specific CD4$^+$ helper and cytotoxic lymphocytes.

Example 4
Determination of the Effect of Modified Tumor Cells in Subjects Previously Exposed to Unmodified Tumor Cells In the previous examples, mice were immunized with modified tumor cells to which they had not been previously exposed. In the case of treating a subject with a pre-existing tumor, the subject will be exposed to unmodified tumor cells for a period of time before exposure to modified tumor cells, and therefore the subject may become tolerized to the unmodified tumor cells.

To determine whether the modified tumor cells of the invention are effective in overcoming tolerance and inducing an anti-tumor T cell response in a subject, mice are inoculated with increasing amounts of wild-type SaI tumor cells which have been irradiated with 10,000 rads. Doses of tumor cells in the range of $1 \times 10^4$ to $1 \times 10^6$ cells can be inoculated. Tumor cells irradiated in this way survive for up to two months in the recipient mice, sufficient time for tolerance to the tumor cells to be induced in the mice. After two months exposure to the wild-type tumor cells, mice are injected simultaneously with wild-type tumor cells into the flank of one hind leg and with tumor cells modified to express B7 (eg. SaI/A$^K$tr/B7-1) into the flank of the opposite hind leg. As a control, mice are injected with wild-type tumor cells into both flanks. Tumor cell doses in the range of $1 \times 10^4$ to $1 \times 10^6$ cells are used for challenges. Tumor growth is assessed by measuring the size of a tumor which grows at the site of injection. The ability of B7-modified tumor cells to induce anti-tumor immunity, and therefore overcome any possible tolerance to the tumor cells in the mice, is determined by the ability of B7-modified tumor cells injected into one flank to prevent growth of wild-type tumor cells in the opposite flank, as compared to when wild-type tumor cells are injected into both flanks.

Alternatively, the ability of B7-modified tumor cells to overcome potential tolerance to unmodified tumor cells is assessed by an adoptive transfer experiment. A mouse is injected intraperitoneally with a low dose, e.g. $1\times10^4$ cells, of wild-type SaI cells and the tumor cells are allowed to grow for three weeks, at which time the mouse is sacrificed and spleen cells from the mouse are harvested. These spleen cells are injected intraperitoneally into a recipient, syngeneic mouse which has been lethally irradiated to destroy its endogenous immune system. The adoptively transferred spleen cells reconstitute the recipient mouse with an immune system which has been previously exposed to wild-type tumor cells. Following spleen cell transfer, the recipient mouse is then challenged with wild-type tumor cells injected into the flank of one hind leg and with B7-modified tumor cells injected into the flank of the opposite hind leg. Tumor cell doses in the range of $1\times10^4$ to $1\times10^6$ cells are used for challenges. The ability of B7-modified tumor cells to induce anti-tumor immunity is determined by the ability of B7-modified tumor cells injected into one flank to prevent the growth of wild-type tumor cells injected into the opposite flank.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. An isolated mammalian tumor cell transfected with an exogenous nucleic acid molecule encoding a mammalian B7 molecule, wherein said molecule is expressed by said tumor cell and wherein said B7 molecule has the ability to costimulate a T cell and the ability to bind CD28 or CTLA4 ligand.

2. The tumor cell of claim 1 which expresses an MHC class II molecule.

3. The tumor cell of claim 1 which expresses an MHC class I molecule.

4. The tumor cell of claim 1 which normally expresses an MHC class II associated protein, the invariant chain, and wherein expression of the invariant chain is inhibited.

5. The tumor cell of claim 1 wherein the exogenous nucleic acid is a cDNA in a recombinant expression vector.

6. The tumor cell of claim 5 further transfected with at least one exogenous nucleic acid molecule encoding:

(a) at least one MHC class II α chain protein, and (b) at least one MHC class II chain protein, wherein said MHC class II α chain protein(s) and said MHC class II β chain protein(s) is expressed by said tumor cell.

7. The tumor cell of claim 6 which does not express MHC class II molecules prior to transfection of the exogenous nucleic acid molecule encoding said MHC class II α chain protein(s) and said MHC class II β chain protein(s) into the tumor cell.

8. The tumor cell of claim 1 further transfected with at least one nucleic acid molecule encoding at least one MHC class I α chain protein wherein said MHC class I protein(s) is expressed by the tumor cell.

9. The tumor cell of claim 8 further transfected with an exogenous nucleic acid molecule encoding a β-2 microglobulin protein, wherein said β2 microglobulin protein is expressed by the tumor cell.

10. The rumor cell of claim 4 wherein expression of the invariant chain is inhibited by transfection of the tumor cell with a nucleic acid which is antisense to a regulatory or a coding region of the invariant chain gene.

11. The tumor cell of claim 1 which is a sarcoma.

12. The tumor cell of claim 1 which is a lymphoma.

13. The tumor cell of claim 1 which is selected from a group consisting of a melanoma, a neuroblastoma, a leukemia and a carcinoma.

14. An isolated mammalian sarcoma cell transfected with an exogenous nucleic acid molecule encoding a mammalian B7 molecule wherein said B7 molecule is expressed in said tumor cell and wherein said B7 molecule has the ability to costimulate a T cell and the ability to bind a CD28 or CTLA4 ligand.

15. The sarcoma cell of claim 14 which expresses an MHC class II molecule.

16. The sarcoma cell of claim 15 which expresses an MHC class I molecule.

17. The tumor cell as in any one of claims 1, 2, 5, 13, or 14 wherein the cell is further transfected with an exogenous nucleic acid molecule encoding a cytokine, wherein said cytokine is expressed in said tumor cell.

18. A composition comprising an amount of the tumor cells of any of claims 1, 2, 5, 6, 12, 13, or 14, and a physiologically acceptable crier.

* * * * *

UNITED STATES PATENT AND TRADEMARK OFFICE
CERTIFICATE OF CORRECTION

PATENT NO. : 5,858,776
DATED : January 12, 1999
INVENTOR(S) : Suzanne Ostrand-Rosenberg et al.

It is certified that error appears in the above-indentified patent and that said Letters Patent is hereby corrected as shown below:

In claim 18, the word "crier" should read "carrier".

Signed and Sealed this

Fifteenth Day of June, 1999

Attest:

Q. TODD DICKINSON

*Attesting Officer*      *Acting Commissioner of Patents and Trademarks*

UNITED STATES PATENT AND TRADEMARK OFFICE
CERTIFICATE OF CORRECTION

PATENT NO.    : 5,858,776
DATED         : January 12, 1999
INVENTOR(S)   : Suzanne Ostrand-Rosenberg et al.

It is certified that error appears in the above-identified patent and that said Letters Patent is hereby corrected as shown below:

Title page,
Item [73], Assignee, "Repligen Corporation" needs to be removed as an Assignee. Assignees of the patent should read: -- President and Fellows of Harvard College; and Dana-Farber Cancer Institute. --

Column 39,
Line 53, the word "withan" should read -- with an --.
Line 57, the word "bind CD28" should read -- bind a CD28 --.

Column 41,
Line 3, the word "rumor" should read -- tumor --.

Signed and Sealed this

First Day of October, 2002

Attest:

Attesting Officer

JAMES E. ROGAN
*Director of the United States Patent and Trademark Office*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1491 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: no ( i v ) ANTI-SENSE: no ( v i ) ORIGINAL SOURCE:
        ( A ) ORGANISM: Homo sapien
        ( F ) TISSUE TYPE: lymphoid
        ( G ) CELL TYPE: B cell
        ( H ) CELL LINE: Raji ( v i i ) IMMEDIATE SOURCE:
        ( A ) LIBRARY: cDNA in pCDM8 vector
        ( B ) CLONE: B7, Raji clone #13

( v i i i ) POSITION IN GENOME:
        ( A ) CHROMOSOME/SEGMENT: 3

( i x ) FEATURE:
        ( A ) NAME/KEY: Open reading frame (translated region)
        ( B ) LOCATION: 318 to 1181 bp
        ( C ) IDENTIFICATION METHOD: similarity to other pattern ( i x ) FEATURE:
        ( A ) NAME/KEY: Alternate polyadenylation signal
        ( B ) LOCATION: 1474 to 1479 bp
        ( C ) IDENTIFICATION METHOD: similarity to other pattern ( x ) PUBLICATION INFORMATION:
        ( A ) AUTHORS: FREEMAN, GORDON J.
            FREEDMAN, ARNOLD S.
            SEGIL, JEFFREY M.
            LEE, GRACE
            WHITMAN, JAMES F.
            NADLER, LEE M.
        ( B ) TITLE: B7, A New Member Of The Ig Superfamily With
            Unique Expression On Activated And Neoplastic B Cells
        ( C ) JOURNAL: The Journal of Immunology
        ( D ) VOLUME: 143
        ( E ) ISSUE: 8
        ( F ) PAGES: 2714-2722
        ( G ) DATE: 15-OCT-1989
        ( H ) RELEVANT RESIDUES IN SEQ ID NO:1: FROM 1 TO 1491

( x i ) SEQUENCE DESCRIPTION: SEQ ID NO:1:

```
CCAAAGAAAA AGTGATTTGT CATTGCTTTA TAGACTGTAA GAAGAGAACA TCTCAGAAGT       60

GGAGTCTTAC CCTGAAATCA AAGGATTTAA AGAAAAAGTG GAATTTTCT  TCAGCAAGCT      120

GTGAAACTAA ATCCACAACC TTTGGAGACC CAGGAACACC CTCCAATCTC TGTGTGTTTT      180

GTAAACATCA CTGGAGGGTC TTCTACGTGA GCAATTGGAT TGTCATCAGC CCTGCCTGTT      240

TTGCACCTGG GAAGTGCCCT GGTCTTACTT GGGTCCAAAT TGTTGGCTTT CACTTTTGAC      300

CCTAAGCATC TGAAGCC ATG GGC CAC ACA CGG AGG CAG GGA ACA TCA CCA TCC     353
                    Met Gly His Thr Arg Arg Gln Gly Thr Ser Pro Ser
                                    -30                     -25

AAG TGT CCA TAC CTG AAT TTC TTT CAG CTC TTG GTG CTG GCT GGT CTT        401
Lys Cys Pro Tyr Leu Asn Phe Phe Gln Leu Leu Val Leu Ala Gly Leu
        -20                 -15                 -10

TCT CAC TTC TGT TCA GGT GTT ATC CAC GTG ACC AAG GAA GTG AAA GAA        449
Ser His Phe Cys Ser Gly Val Ile His Val Thr Lys Glu Val Lys Glu
        -5                   1                   5                  10

GTG GCA ACG CTG TCC TGT GGT CAC AAT GTT TCT GTT GAA GAG CTG GCA        497
Val Ala Thr Leu Ser Cys Gly His Asn Val Ser Val Glu Glu Leu Ala
                15                  20                  25

CAA ACT CGC ATC TAC TGG CAA AAG GAG AAG AAA ATG GTG CTG ACT ATG        545
Gln Thr Arg Ile Tyr Trp Gln Lys Glu Lys Lys Met Val Leu Thr Met
            30                  35                  40

ATG TCT GGG GAC ATG AAT ATA TGG CCC GAG TAC AAG AAC CGG ACC ATC        593
Met Ser Gly Asp Met Asn Ile Trp Pro Glu Tyr Lys Asn Arg Thr Ile
        45                  50                  55

TTT GAT ATC ACT AAT AAC CTC TCC ATT GTG ATC CTG GCT CTG CGC CCA        641
Phe Asp Ile Thr Asn Asn Leu Ser Ile Val Ile Leu Ala Leu Arg Pro
    60                  65                  70

TCT GAC GAG GGC ACA TAC GAG TGT GTT GTT CTG AAG TAT GAA AAA GAC        689
Ser Asp Glu Gly Thr Tyr Glu Cys Val Val Leu Lys Tyr Glu Lys Asp
75                  80                  85                  90

GCT TTC AAG CGG GAA CAC CTG GCT GAA GTG ACG TTA TCA GTC AAA GCT        737
Ala Phe Lys Arg Glu His Leu Ala Glu Val Thr Leu Ser Val Lys Ala
        95                  100                 105

GAC TTC CCT ACA CCT AGT ATA TCT GAC TTT GAA ATT CCA ACT TCT AAT        785
Asp Phe Pro Thr Pro Ser Ile Ser Asp Phe Glu Ile Pro Thr Ser Asn
            110                 115                 120

ATT AGA AGG ATA ATT TGC TCA ACC TCT GGA GGT TTT CCA GAG CCT CAC        833
Ile Arg Arg Ile Ile Cys Ser Thr Ser Gly Gly Phe Pro Glu Pro His
        125                 130                 135

CTC TCC TGG TTG GAA AAT GGA GAA GAA TTA AAT GCC ATC AAC ACA ACA        881
Leu Ser Trp Leu Glu Asn Gly Glu Glu Leu Asn Ala Ile Asn Thr Thr
    140                 145                 150

GTT TCC CAA GAT CCT GAA ACT GAG CTC TAT GCT GTT AGC AGC AAA CTG        929
Val Ser Gln Asp Pro Glu Thr Glu Leu Tyr Ala Val Ser Ser Lys Leu
155                 160                 165                 170

GAT TTC AAT ATG ACA ACC AAC CAC AGC TTC ATG TGT CTC ATC AAG TAT        977
Asp Phe Asn Met Thr Thr Asn His Ser Phe Met Cys Leu Ile Lys Tyr
        175                 180                 185

GGA CAT TTA AGA GTG AAT CAG ACC TTC AAC TGG AAT ACA ACC AAG CAA       1025
Gly His Leu Arg Val Asn Gln Thr Phe Asn Trp Asn Thr Thr Lys Gln
            190                 195                 200

GAG CAT TTT CCT GAT AAC CTG CTC CCA TCC TGG GCC ATT ACC TTA ATC       1073
Glu His Phe Pro Asp Asn Leu Leu Pro Ser Trp Ala Ile Thr Leu Ile
        205                 210                 215

TCA GTA AAT GGA ATT TTT GTG ATA TGC TGC CTG ACC TAC TGC TTT GCC       1121
Ser Val Asn Gly Ile Phe Val Ile Cys Cys Leu Thr Tyr Cys Phe Ala
    220                 225                 230
```

| CCA | AGA | TGC | AGA | GAG | AGA | AGG | AGG | AAT | GAG | AGA | TTG | AGA | AGG | GAA | AGT | 1169 |
| Pro | Arg | Cys | Arg | Glu | Arg | Arg | Arg | Asn | Glu | Arg | Leu | Arg | Arg | Glu | Ser | |
| 235 | | | | 240 | | | | | 245 | | | | | 250 | | |

| GTA | CGC | CCT | GTA | TAACAGTGTC | CGCAGAAGCA | AGGGGCTGAA | AAGATCTGAA | 1221 |
| Val | Arg | Pro | Val | | | | | |

GGTAGCCTCC GTCATCTCTT CTGGGATACA TGGATCGTGG GGATCATGAG GCATTCTTCC 1281

CTTAACAAAT TTAAGCTGTT TTACCCACTA CCTCACCTTC TTAAAAACCT CTTTCAGATT 1341

AAGCTGAACA GTTACAAGAT GGCTGGCATC CCTCTCCTTT CTCCCCATAT GCAATTTGCT 1401

TAATGTAACC TCTTCTTTTG CCATGTTTCC ATTCTGCCAT CTTGAATTGT CTTGTCAGCC 1461

AATTCATTAT CTATTAAACA CTAATTTGAG 1491

( 2 ) INFORMATION FOR SEQ ID NO:2:

( i ) SEQUENCE CHARACTERISTICS:
        ( A ) LENGTH: 288 amino acids
        ( B ) TYPE: amino acid
        ( C ) TOPOLOGY: linear ( i i ) MOLECULE TYPE: protein
        ( A ) DESCRIPTION: B cell activation antigen; natural ligand
            for CD28 T cell surface antigen; transmembrane protein ( i x ) FEATURE:
        ( A ) NAME/KEY: signal sequence
        ( B ) LOCATION: -34 to -1
        ( C ) IDENTIFICATION METHOD: amino terminal sequencing of
            soluble protein
        ( D ) OTHER INFORMATION: hydrophobic ( i x ) FEATURE:
        ( A ) NAME/KEY: extracellular domain
        ( B ) LOCATION: 1 to 208
        ( C ) IDENTIFICATION METHOD: similarity with known
            sequence ( i x ) FEATURE:
        ( A ) NAME/KEY: transmembrane domain
        ( B ) LOCATION: 209 to 235
        ( C ) IDENTIFICATION METHOD: similarity with known
            sequence ( i x ) FEATURE:
        ( A ) NAME/KEY: intracellular domain
        ( B ) LOCATION: 236 to 254
        ( C ) IDENTIFICATION METHOD: similarity with known
            sequence ( i x ) FEATURE:
        ( A ) NAME/KEY: N-linked glycosylation
        ( B ) LOCATION: 19 to 21
        ( C ) IDENTIFICATION METHOD: similarity with known
            sequence ( i x ) FEATURE:
        ( A ) NAME/KEY: N-linked glycosylation
        ( B ) LOCATION: 55 to 57
        ( C ) IDENTIFICATION METHOD: similarity with known
            sequence ( i x ) FEATURE:
        ( A ) NAME/KEY: N-linked glycosylation
        ( B ) LOCATION: 64 to 66
        ( C ) IDENTIFICATION METHOD: similarity with known
            sequence ( i x ) FEATURE:
        ( A ) NAME/KEY: N-linked glycosylation
        ( B ) LOCATION: 152 to 154
        ( C ) IDENTIFICATION METHOD: similarity with known
            sequence ( i x ) FEATURE:

(A) NAME/KEY: N-linked glycosylation
    (B) LOCATION: 173 to 175
    (C) IDENTIFICATION METHOD: similarity with known
        sequence (ix) FEATURE:
    (A) NAME/KEY: N-linked glycosylation
    (B) LOCATION: 177 to 179
    (C) IDENTIFICATION METHOD: similarity with known
        sequence (ix) FEATURE:
    (A) NAME/KEY: N-linked glycosylation
    (B) LOCATION: 192 to 194
    (C) IDENTIFICATION METHOD: similarity with known
        sequence (ix) FEATURE:
    (A) NAME/KEY: N-linked glycosylation
    (B) LOCATION: 198 to 200
    (C) IDENTIFICATION METHOD: similarity with known
        sequence (ix) FEATURE:
    (A) NAME/KEY: Ig V-set domain
    (B) LOCATION: 1 to 104
    (C) IDENTIFICATION METHOD: similarity with known
        sequence (ix) FEATURE:
    (A) NAME/KEY: Ig C-set domain
    (B) LOCATION: 105 to 202
    (C) IDENTIFICATION METHOD: similarity with known
        sequence (x) PUBLICATION INFORMATION:
    (A) AUTHORS: FREEMAN, GORDON J.
        FREEDMAN, ARNOLD S.
        SEGIL, JEFFREY M.
        LEE, GRACE
        WHITMAN, JAMES F.
        NADLER, LEE M.
    (B) TITLE: B7, A New Member Of The Ig Superfamily With
        Unique Expression On Activated And Neoplastic B Cells
    (C) JOURNAL: The Journal of Immunology
    (D) VOLUME: 143
    (E) ISSUE: 8
    (F) PAGES: 2714-2722
    (G) DATE: 15-OCT-1989
    (H) RELEVANT RESIDUES IN SEQ ID NO:2: From -26 to 262

(xi) SEQUENCE DESCRIPTION: SEQ ID NO:2:

```
Met Gly His Thr Arg Arg Gln Gly Thr Ser Pro Ser Lys Cys Pro Tyr
            -30              -25              -20

Leu Asn Phe Phe Gln Leu Leu Val Leu Ala Gly Leu Ser His Phe Cys
        -15              -10                   -5

Ser Gly Val Ile His Val Thr Lys Glu Val Lys Glu Val Ala Thr Leu
    -1   1               5              10

Ser Cys Gly His Asn Val Ser Val Glu Glu Leu Ala Gln Thr Arg Ile
15              20              25              30

Tyr Trp Gln Lys Glu Lys Lys Met Val Leu Thr Met Met Ser Gly Asp
                35              40                   45

Met Asn Ile Trp Pro Glu Tyr Lys Asn Arg Thr Ile Phe Asp Ile Thr
            50              55              60

Asn Asn Leu Ser Ile Val Ile Leu Ala Leu Arg Pro Ser Asp Glu Gly
        65              70              75

Thr Tyr Glu Cys Val Val Leu Lys Tyr Glu Lys Asp Ala Phe Lys Arg
    80              85              90

Glu His Leu Ala Glu Val Thr Leu Ser Val Lys Ala Asp Phe Pro Thr
95              100             105             110
```

| Pro | Ser | Ile | Ser | Asp | Phe | Glu | Ile | Pro | Thr | Ser | Asn | Ile | Arg | Arg | Ile |
|-----|-----|-----|-----|-----|-----|-----|-----|-----|-----|-----|-----|-----|-----|-----|-----|
|     |     |     |     | 115 |     |     |     |     | 120 |     |     |     |     | 125 |     |
| Ile | Cys | Ser | Thr | Ser | Gly | Gly | Phe | Pro | Glu | Pro | His | Leu | Ser | Trp | Leu |
|     |     |     | 130 |     |     |     |     | 135 |     |     |     |     | 140 |     |     |
| Glu | Asn | Gly | Glu | Glu | Leu | Asn | Ala | Ile | Asn | Thr | Thr | Val | Ser | Gln | Asp |
|     |     | 145 |     |     |     |     | 150 |     |     |     |     | 155 |     |     |     |
| Pro | Glu | Thr | Glu | Leu | Tyr | Ala | Val | Ser | Ser | Lys | Leu | Asp | Phe | Asn | Met |
|     | 160 |     |     |     |     | 165 |     |     |     |     | 170 |     |     |     |     |
| Thr | Thr | Asn | His | Ser | Phe | Met | Cys | Leu | Ile | Lys | Tyr | Gly | His | Leu | Arg |
| 175 |     |     |     |     | 180 |     |     |     |     | 185 |     |     |     |     | 190 |
| Val | Asn | Gln | Thr | Phe | Asn | Trp | Asn | Thr | Thr | Lys | Gln | Glu | His | Phe | Pro |
|     |     |     |     | 195 |     |     |     |     | 200 |     |     |     |     | 205 |     |
| Asp | Asn | Leu | Leu | Pro | Ser | Trp | Ala | Ile | Thr | Leu | Ile | Ser | Val | Asn | Gly |
|     |     |     | 210 |     |     |     |     | 215 |     |     |     |     | 220 |     |     |
| Ile | Phe | Val | Ile | Cys | Cys | Leu | Thr | Tyr | Cys | Phe | Ala | Pro | Arg | Cys | Arg |
|     |     | 225 |     |     |     |     | 230 |     |     |     |     | 235 |     |     |     |
| Glu | Arg | Arg | Arg | Asn | Glu | Arg | Leu | Arg | Arg | Glu | Ser | Val | Arg | Pro | Val |
|     | 240 |     |     |     |     | 245 |     |     |     |     | 250 |     |     |     |     |

( 2 ) INFORMATION FOR SEQ ID NO:3:

( i ) SEQUENCE CHARACTERISTICS:
        ( A ) LENGTH: 1716 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: no ( v i ) ORIGINAL SOURCE:
        ( A ) ORGANISM: Mus musculus
        ( D ) DEVELOPMENTAL STAGE: germ line
        ( F ) TISSUE TYPE: lymphoid
        ( G ) CELL TYPE: B lymphocyte
        ( H ) CELL LINE: 70Z and A20

( v i i ) IMMEDIATE SOURCE:
        ( A ) LIBRARY: cDNA in pCDM8 vector
        ( B ) CLONE: B7 #'s 1 and 29

( i x ) FEATURE:
        ( A ) NAME/KEY: translated region
        ( B ) LOCATION: 249 to 1166 bp
        ( C ) IDENTIFICATION METHOD: similarity to other pattern ( i x ) FEATURE:
        ( A ) NAME/KEY: Alternate ATG initiation codons
        ( B ) LOCATION: 225 to 227 and 270 to 272
        ( C ) IDENTIFICATION METHOD: similarity to other pattern ( x i ) SEQUENCE DESCRIPTION: SEQ ID NO:3:

```
GAGTTTTATA  CCTCAATAGA  CTCTTACTAG  TTTCTCTTTT  TCAGGTTGTG  AAACTCAACC       60

TTCAAAGACA  CTCTGTTCCA  TTTCTGTGGA  CTAATAGGAT  CATCTTTAGC  ATCTGCCGGG      120

TGGATGCCAT  CCAGGCTTCT  TTTTCTACAT  CTCTGTTTCT  CGATTTTGT  GAGCCTAGGA       180

GGTGCCTAAG  CTCCATTGGC  TCTAGATTCC  TGGCTTTCCC  CATCATGTTC  TCCAAAGCAT      240

CTGAAGCT  ATG  GCT  TGC  AAT  TGT  CAG  TTG  ATG  CAG  GAT  ACA  CCA  CTC  CTC      290
          Met  Ala  Cys  Asn  Cys  Gln  Leu  Met  Gln  Asp  Thr  Pro  Leu  Leu
          -35                           -30                       -25

AAG  TTT  CCA  TGT  CCA  AGG  CTC  AAT  CTT  CTC  TTT  GTG  CTG  CTG  ATT  CGT      338
Lys  Phe  Pro  Cys  Pro  Arg  Leu  Ile  Leu  Leu  Phe  Val  Leu  Leu  Ile  Arg
              -20                    -15                        -10

CTT  TCA  CAA  GTG  TCT  TCA  GAT  GTT  GAT  GAA  CAA  CTG  TCC  AAG  TCA  GTG      386
```

```
Leu Ser Gln Val Ser Ser Asp Val Asp Glu Gln Leu Ser Lys Ser Val
    -5                      -1   1                    5

AAA GAT AAG GTA TTG CTG CCT TGC CGT TAC AAC TCT CCT CAT GAA GAT     434
Lys Asp Lys Val Leu Leu Pro Cys Arg Tyr Asn Ser Pro His Glu Asp
 10              15                  20              25

GAG TCT GAA GAC CGA ATC TAC TGG CAA AAA CAT GAC AAA GTG GTG CTG     482
Glu Ser Glu Asp Arg Ile Tyr Trp Gln Lys His Asp Lys Val Val Leu
                 30                  35                  40

TCT GTC ATT GCT GGG AAA CTA AAA GTG TGG CCC GAG TAT AAG AAC CGG     530
Ser Val Ile Ala Gly Lys Leu Lys Val Trp Pro Glu Tyr Lys Asn Arg
             45                  50                  55

ACT TTA TAT GAC AAC ACT ACC TAC TCT CTT ATC ATC CTG GGC CTG GTC     578
Thr Leu Tyr Asp Asn Thr Thr Tyr Ser Leu Ile Ile Leu Gly Leu Val
             60                  65                  70

CTT TCA GAC CGG GGC ACA TAC AGC TGT GTC GTT CAA AAG AAG GAA AGA     626
Leu Ser Asp Arg Gly Thr Tyr Ser Cys Val Val Gln Lys Lys Glu Arg
     75                  80                  85

GGA ACG TAT GAA GTT AAA CAC TTG GCT TTA GTA AAG TTG TCC ATC AAA     674
Gly Thr Tyr Glu Val Lys His Leu Ala Leu Val Lys Leu Ser Ile Lys
 90                  95                 100                 105

GCT GAC TTC TCT ACC CCC AAC ATA ACT GAG TCT GGA AAC CCA TCT GCA     722
Ala Asp Phe Ser Thr Pro Asn Ile Thr Glu Ser Gly Asn Pro Ser Ala
             110                 115                 120

GAC ACT AAA AGG ATT ACC TGC TTT GCT TCC GGG GGT TTC CCA AAG CCT     770
Asp Thr Lys Arg Ile Thr Cys Phe Ala Ser Gly Gly Phe Pro Lys Pro
         125                 130                 135

CGC TTC TCT TGG TTG GAA AAT GGA AGA GAA TTA CCT GGC ATC AAT ACG     818
Arg Phe Ser Trp Leu Glu Asn Gly Arg Glu Leu Pro Gly Ile Asn Thr
         140                 145                 150

ACA ATT TCC CAG GAT CCT GAA TCT GAA TTG TAC ACC ATT AGT AGC CAA     866
Thr Ile Ser Gln Asp Pro Glu Ser Glu Leu Tyr Thr Ile Ser Ser Gln
 155                 160                 165

CTA GAT TTC AAT ACG ACT CGC AAC CAC ACC ATT AAG TGT CTC ATT AAA     914
Leu Asp Phe Asn Thr Thr Arg Asn His Thr Ile Lys Cys Leu Ile Lys
 170                 175                 180                 185

TAT GGA GAT GCT CAC GTG TCA GAG GAC TTC ACC TGG GAA AAA CCC CCA     962
Tyr Gly Asp Ala His Val Ser Glu Asp Phe Thr Trp Glu Lys Pro Pro
                 190                 195                 200

GAA GAC CCT CCT GAT AGC AAG AAC ACA CTT GTG CTC TTT GGG GCA GGA    1010
Glu Asp Pro Pro Asp Ser Lys Asn Thr Leu Val Leu Phe Gly Ala Gly
             205                 210                 215

TTC GGC GCA GTA ATA ACA GTC GTC GTC ATC GTT GTC ATC ATC AAA TGC    1058
Phe Gly Ala Val Ile Thr Val Val Val Ile Val Val Ile Ile Lys Cys
         220                 225                 230

TTC TGT AAG CAC AGA AGC TGT TTC AGA AGA AAT GAG GCA AGC AGA GAA    1106
Phe Cys Lys His Arg Ser Cys Phe Arg Arg Asn Glu Ala Ser Arg Glu
         235                 240                 245

ACA AAC AAC AGC CTT ACC TTC GGG CCT GAA GAA GCA TTA GCT GAA CAG    1154
Thr Asn Asn Ser Leu Thr Phe Gly Pro Glu Glu Ala Leu Ala Glu Gln
 250                 255                 260                 265

ACC GTC TTC CTT TAGTTCTTCT CTGTCCATGT GGGATACATG GTATTATGTG        1206
Thr Val Phe Leu

GCTCATGAGG TACAATCTTT CTTTCAGCAC CGTGCTAGCT GATCTTTCGG ACAACTTGAC  1266

ACAAGATAGA GTTAACTGGG AAGAGAAAGC CTTGAATGAG GATTTCTTTC CATCAGGAAG  1326

CTACGGGCAA GTTTGCTGGG CCTTTGATTG CTTGATGACT GAAGTGGAAA GGCTGAGCCC  1386

ACTGTGGGTG GTGCTAGCCC TGGGCAGGGG CAGGTGACCC TGGGTGGTAT AAGAAAAAGA  1446

GCTGTCACTA AAAGGAGAGG TGCCTAGTCT TACTGCAACT TGATATGTCA TGTTTGGTTG  1506
```

| | | | | | |
|---|---|---|---|---|---|
| GTGTCTGTGG | GAGGCCTGCC | CTTTTCTGAA | GAGAAGTGGT | GGGAGAGTGG | ATGGGGTGGG | 1566
| GGCAGAGGAA | AAGTGGGGGA | GAGGGCCTGG | GAGGAGAGGA | GGGAGGGGGA | CGGGGTGGGG | 1626
| GTGGGGAAAA | CTATGGTTGG | GATGTAAAAA | CGGATAATAA | TATAAATATT | AAATAAAAAG | 1686
| AGAGTATTGA | GCAAAAAAAA | AAAAAAAAA | | | | 1716

( 2 ) INFORMATION FOR SEQ ID NO:4:

( i ) SEQUENCE CHARACTERISTICS:
        ( A ) LENGTH: 306 amino acids
        ( B ) TYPE: amino acid
        ( C ) TOPOLOGY: linear ( i i ) MOLECULE TYPE: protein
        ( A ) DESCRIPTION: B lymphocyte activation antigen; Ig
            superfamily member; T cell costimulatory signal
            via activation of CD28 pathways, binds to CD28+
            T cells, transmembrane protein ( i x ) FEATURE:
        ( A ) NAME/KEY: signal sequence
        ( B ) LOCATION: -37 to -1
        ( C ) IDENTIFICATION METHOD: similarity with known
            sequence
        ( D ) OTHER INFORMATION: hydrophobic ( i x ) FEATURE:
        ( A ) NAME/KEY: extracellular domain
        ( B ) LOCATION: 1 to 210
        ( C ) IDENTIFICATION METHOD: similarity with known
            sequence ( i x ) FEATURE:
        ( A ) NAME/KEY: transmembrane domain
        ( B ) LOCATION: 211 to 235
        ( C ) IDENTIFICATION METHOD: similarity with known
            sequence ( i x ) FEATURE:
        ( A ) NAME/KEY: intracellular (cytoplasmic) domain
        ( B ) LOCATION: 236 to 269
        ( C ) IDENTIFICATION METHOD: similarity with known
            sequence ( i x ) FEATURE:
        ( A ) NAME/KEY: Ig V-set domain
        ( B ) LOCATION: 1 to 105
        ( C ) IDENTIFICATION METHOD: similarity with known
            sequence ( i x ) FEATURE:
        ( A ) NAME/KEY: Ig C-set domain
        ( B ) LOCATION: 106 to 199
        ( C ) IDENTIFICATION METHOD: similarity with known
            sequence ( x ) PUBLICATION INFORMATION:
        ( A ) AUTHORS: FREEMAN, GORDON J.
            GRAY, GARY S.
            GIMMI, CLAUDE D.
            LOMBARD, DAVID B.
            ZHOU, LIANG- JI
            WHITE, MICHAEL
            FINGEROTH, JOYCE D.
            GRIBBEN, JOHN G.
            NADLER, LEE M.
        ( B ) TITLE: Structure, Expression, and T Cell Costimulatory
            Activity Of The Murine Homologue Of The Human B
            Lymphocyte Activation Antigen B7
        ( C ) JOURNAL: Journal of Experimental Medicine
        ( D ) VOLUME:
        ( E ) ISSUE:
        ( F ) PAGES:
        ( G ) DATE: IN PRESS
        ( H ) RELEVANT RESIDUES IN SEQ ID NO:4: From -37 to 269

( x i ) SEQUENCE DESCRIPTION: SEQ ID NO:4:

-continued

| | | | | | | | | | | | | | | |
|---|---|---|---|---|---|---|---|---|---|---|---|---|---|---|
| Met | Ala | Cys -35 | Asn | Cys | Gln | Leu | Met -30 | Gln | Asp | Thr | Pro | Leu -25 | Leu | Lys | Phe |
| Pro | Cys -20 | Pro | Arg | Leu | Ile | Leu -15 | Leu | Phe | Val | Leu | Leu -10 | Ile | Arg | Leu | Ser |
| Gln -5 | Val | Ser | Ser | Asp -1 | Val 1 | Asp | Glu | Gln | Leu 5 | Ser | Lys | Ser | Val | Lys 10 | Asp |
| Lys | Val | Leu | Leu 15 | Pro | Cys | Arg | Tyr | Asn 20 | Ser | Pro | His | Glu | Asp 25 | Glu | Ser |
| Glu | Asp | Arg 30 | Ile | Tyr | Trp | Gln | Lys 35 | His | Asp | Lys | Val | Val 40 | Leu | Ser | Val |
| Ile | Ala 45 | Gly | Lys | Leu | Lys | Val 50 | Trp | Pro | Glu | Tyr | Lys 55 | Asn | Arg | Thr | Leu |
| Tyr 60 | Asp | Asn | Thr | Thr | Tyr 65 | Ser | Leu | Ile | Ile | Leu 70 | Gly | Leu | Val | Leu | Ser 75 |
| Asp | Arg | Gly | Thr | Tyr 80 | Ser | Cys | Val | Val | Gln 85 | Lys | Lys | Glu | Arg | Gly 90 | Thr |
| Tyr | Gly | Val | Lys 95 | His | Leu | Ala | Leu | Val 100 | Lys | Leu | Ser | Ile | Lys 105 | Ala | Asp |
| Phe | Ser | Thr 110 | Pro | Asn | Ile | Thr | Glu 115 | Ser | Gly | Asn | Pro | Ser 120 | Ala | Asp | Thr |
| Lys | Arg 125 | Ile | Thr | Cys | Phe | Ala 130 | Ser | Gly | Gly | Phe | Pro 135 | Lys | Pro | Arg | Phe |
| Ser 140 | Trp | Leu | Glu | Asn | Gly 145 | Arg | Glu | Leu | Pro | Gly 150 | Ile | Asn | Thr | Thr | Ile 155 |
| Ser | Gln | Asp | Pro | Glu 160 | Ser | Glu | Leu | Tyr | Thr 165 | Ile | Ser | Ser | Gln | Leu 170 | Asp |
| Phe | Asn | Thr | Thr 175 | Arg | Asn | His | Thr | Ile 180 | Lys | Cys | Leu | Ile | Lys 185 | Tyr | Gly |
| Asp | Ala | His 190 | Val | Ser | Glu | Asp | Phe 195 | Thr | Trp | Glu | Lys | Pro 200 | Pro | Glu | Asp |
| Pro | Pro 205 | Asp | Ser | Lys | Asn | Thr 210 | Leu | Val | Leu | Phe | Gly 215 | Ala | Gly | Phe | Gly |
| Ala 220 | Val | Ile | Thr | Val | Val 225 | Val | Ile | Val | Val | Ile 230 | Ile | Lys | Cys | Phe | Cys 235 |
| Lys | His | Arg | Ser | Cys 240 | Phe | Arg | Arg | Asn | Glu 245 | Ala | Ser | Arg | Glu | Thr 250 | Asn |
| Asn | Ser | Leu | Thr 255 | Phe | Gly | Pro | Glu | Glu 260 | Ala | Leu | Ala | Glu | Gln 265 | Thr | Val |
| Phe | Leu | | | | | | | | | | | | | | |